US012633303B2

(12) United States Patent
Shpak et al.

(10) Patent No.: US 12,633,303 B2
(45) Date of Patent: May 19, 2026

(54) METHOD AND AN ELECTRONIC DEVICE FOR RECORDING BODILY SOUNDS

(71) Applicant: SPARROW ACOUSTICS INC., Lucasville (CA)

(72) Inventors: Yaroslav Shpak, Kiev (UA); Maksim Davydov, Fanipol (BY)

(73) Assignee: SPARROW ACOUSTICS INC., Lucasville (CA)

( * ) Notice: Subject to any disclaimer, the term of this patent is extended or adjusted under 35 U.S.C. 154(b) by 0 days.

(21) Appl. No.: 18/482,387

(22) Filed: Oct. 6, 2023

(65) Prior Publication Data

US 2024/0046954 A1 Feb. 8, 2024

Related U.S. Application Data

(60) Division of application No. 18/086,021, filed on Dec. 21, 2022, now Pat. No. 11,817,116, which is a
(Continued)

(51) Int. Cl.
*G10L 25/00* (2013.01)
*A61B 5/08* (2006.01)
(Continued)

(52) U.S. Cl.
CPC ............... *G10L 25/66* (2013.01); *A61B 7/04* (2013.01); *G10L 25/03* (2013.01); *G16H 40/67* (2018.01);
(Continued)

(58) Field of Classification Search
None
See application file for complete search history.

(56) References Cited

U.S. PATENT DOCUMENTS 4,094,304 A 6/1978 Wright
4,792,145 A 12/1988 Eisenberg et al.
(Continued)

FOREIGN PATENT DOCUMENTS

CN 102125442 A 7/2011
CN 201977775 U 9/2011
(Continued)

OTHER PUBLICATIONS

Bentley, Peter J. "iStethoscope: a demonstration of the use of mobile devices for auscultation." Mobile Health Technologies: Methods and Protocols. New York, NY: Springer New York, 2014. (Year: 2014).*
(Continued)

*Primary Examiner* — Jialong He
(74) *Attorney, Agent, or Firm* — BCF LLP

(57) ABSTRACT

A method of recording a sound signal by a mobile device is disclosed. The method includes determining, by the mobile device, that an edge of the mobile device is biased against a skin of the operator, the mobile device comprising a microphone located on the edge, and monitoring, by the mobile device, an orientation of the mobile device relative to the skin of the operator. In response to the orientation corresponding to a pre-determined orientation, triggering, by the mobile device, recording of bodily sounds using the microphone. During recording, monitoring, by the mobile device, at least one parameter amongst (i) an orientation parameter of the mobile device, (ii) a sound parameter of the sound signal, and (iii) a pressure parameter of the mobile device. In response to the at least one parameter being outside an acceptable range, triggering, by the mobile device, a feedback signal to the operator.

17 Claims, 14 Drawing Sheets

Related U.S. Application Data continuation of application No. PCT/CA2022/051588, filed on Oct. 26, 2022.

(60) Provisional application No. 63/271,997, filed on Oct. 26, 2021.

(51) Int. Cl.

| | |
|---|---|
| *A61B 7/00* | (2006.01) |
| *A61B 7/04* | (2006.01) |
| *G10L 25/03* | (2013.01) |
| *G10L 25/66* | (2013.01) |
| *G16H 40/67* | (2018.01) |
| *G10K 11/16* | (2006.01) |

(52) U.S. Cl.

CPC ...... *A61B 2562/0204* (2013.01); *G10K 11/16* (2013.01)

(56) References Cited

U.S. PATENT DOCUMENTS

| | | | |
|---|---|---|---|
| 6,873,955 | B1 | 3/2005 | Suzuki et al. |
| 8,200,277 | B2 | 6/2012 | Lee |
| 9,445,763 | B2 | 9/2016 | Davis et al. |
| 9,485,345 | B2 | 11/2016 | Chandrasekaran et al. |
| 9,610,042 | B1 | 4/2017 | Vyshedskiy |
| 9,814,438 | B2 | 11/2017 | Stamatopoulos et al. |
| 9,820,696 | B1 | 11/2017 | Narasimhan |
| 9,848,848 | B2 | 12/2017 | Emmanouilidou et al. |
| 9,866,953 | B2 | 1/2018 | Chong et al. |
| 10,004,473 | B2 | 6/2018 | Tsai et al. |
| 10,098,569 | B2 | 10/2018 | Abeyratne et al. |
| 10,229,754 | B2 | 3/2019 | Cronin et al. |
| 10,993,670 | B2 | 5/2021 | Shute et al. |
| 2005/0078533 | A1 | 4/2005 | Vyshedskiy et al. |
| 2008/0146276 | A1* | 6/2008 | Lee ...................... A61B 5/6887 455/556.1 |
| 2008/0273709 | A1 | 11/2008 | Thiagarajan et al. |
| 2014/0056439 | A1 | 2/2014 | Kim |
| 2014/0371631 | A1 | 12/2014 | Fontana |
| 2015/0104027 | A1* | 4/2015 | Mulumudi ............... A61B 7/04 381/67 |
| 2016/0224312 | A1 | 8/2016 | Wu |
| 2016/0302003 | A1 | 10/2016 | Rahman et al. |
| 2017/0112439 | A1* | 4/2017 | Dubin ................... A61B 5/743 |
| 2017/0235365 | A1* | 8/2017 | Siripurapu .............. G06F 3/015 345/173 |
| 2018/0228468 | A1 | 8/2018 | Adler et al. |
| 2019/0059824 | A1 | 2/2019 | Chen et al. |
| 2019/0109684 | A1 | 4/2019 | Chen et al. |
| 2019/0192047 | A1 | 6/2019 | Stamatopoulos et al. |
| 2020/0152218 | A1* | 5/2020 | Kikuhara ............... H04R 3/005 |
| 2021/0005323 | A1* | 1/2021 | De Bie ................. A61B 5/746 |
| 2021/0059586 | A1* | 3/2021 | Marriott .............. A61B 5/7225 |
| 2021/0235203 | A1* | 7/2021 | Lunner ............... H04R 25/609 |
| 2022/0068505 | A1 | 3/2022 | Junnarkar |

FOREIGN PATENT DOCUMENTS

| | | | | |
|---|---|---|---|---|
| CN | 202026360 | U | 11/2011 | |
| CN | 102512138 | A | 6/2012 | |
| CN | 203408062 | U | 1/2014 | |
| CN | 102112049 | B * | 10/2014 | .............. A61B 5/08 |
| CN | 102685285 | B | 8/2016 | |
| CN | 109589129 | A | 4/2019 | |
| CN | 111820937 | A | 10/2020 | |
| CN | 111883180 | A * | 11/2020 | .............. A61B 7/04 |
| EP | 3416564 | B1 | 6/2020 | |
| JP | 2012512437 | A | 5/2012 | |
| JP | 2013146287 | A | 8/2013 | |
| KR | 102029760 | B1 * | 10/2019 | |
| WO | 2010069885 | A1 | 6/2010 | |
| WO | 2011013881 | A1 | 2/2011 | |
| WO | 2013152022 | A1 | 10/2013 | |
| WO | 2017075601 | A1 | 5/2017 | |
| WO | 2020051546 | A1 | 3/2020 | |
| WO | 2021054742 | A1 | 3/2021 | |

OTHER PUBLICATIONS

Kang, Si-Hyuck, et al. "Cardiac auscultation using smartphones: pilot study." JMIR mHealth and uHealth 6.2 (2018) (Year: 2018).*

Ferreira-Cardoso, Henrique, et al. "Lung auscultation using the smartphone-feasibility study in real-world clinical practice." Sensors 21.14 (Jul. 2021). (Year: 2021).*

Talab, Elhoussine, et al. "Detecting heart anomalies using mobile phones and machine learning." 2019 IEEE 19th International Conference on Bioinformatics and Bioengineering (Bibe). IEEE, 2019. (Year: 2019).*

Steth IO User's Guide, Document No. 11-00-UM-1000-00, Revision E, Oct. 12, 2018, 19 pages.

3M Littmann Brand, Electronic Stethoscope Model 3200 User Manual, 2009, 16 pages.

International Search Report and Written Opinion issued in International application No. PCT/CA2021/051232 on Dec. 9, 2021.

Non-final rejection issued in U.S. Appl. No. 18/086,050 on May 30, 2023.

Supplementary European Search Report issued in European application No. 2186541.7 on Jul. 31, 2024.

Bentley, P.J., iStethoscope: a demonstration of the use of mobile devices for auscultation, Mobile Health TEchnologies: Methods and Protocols (2015), 293-303.

* cited by examiner

Signal without filtering

Amplitude

Time, s

METHOD AND AN ELECTRONIC DEVICE FOR RECORDING BODILY SOUNDS

CROSS-REFERENCE TO RELATED APPLICATIONS

The application is a Divisional of U.S. patent application Ser. No. 18/086,021 filed on Dec. 21, 2022, which is a Continuation of international PCT patent application No. PCT/CA2022/051588 filed on Oct. 26, 2022, and which claimed the benefit of priority of U.S. provisional application No. 63/271,997 filed on Oct. 26, 2021. The contents of the above noted applications are incorporated herein by reference.

FIELD

The present technology relates to sound processing in general, and specifically to methods and electronic devices for processing a waveform.

BACKGROUND

Auscultation has been a key technique in medical diagnosis for centuries. In auscultation, a medical practitioner listens to the internal sounds of the body, typically using a stethoscope. For example, a stethoscope can be used for listening to internal sounds from the heart, lungs, and other organs.

Auscultation is most commonly performed for the purpose of examining the circulatory and respiratory systems, and thus diagnosing conditions of the heart and lungs in particular. In more recent years, electronic stethoscopes and methods of digital processing of body sounds have become available, in order to enhance and supplement the medical practitioner's auditory capabilities.

SUMMARY

It is an object of the present technology to ameliorate at least some of the inconveniences present in the prior art. Embodiments of the present technology may provide and/or broaden the scope of approaches to and/or methods of achieving the aims and objects of the present technology.

A variety of stethoscopes are available for the auscultation of bodily sounds. Many stethoscopes have a separate bell and diaphragm. The bell is most effective at transmitting lower frequency sounds, while the diaphragm is most effective at transmitting higher frequency sounds. Some stethoscopes combine these functions into a single surface. For example, the intensity of pressure of the stethoscope against the skin determines whether the stethoscope functions as a bell or a diaphragm. In addition, pressing the bell more firmly against the skin alters the frequencies that are loudest towards those of a diaphragm, such that higher frequency sounds become louder and lower frequency sounds become softer. Therefore, a stethoscope can be operated in either a "bell mode" for better capturing a low-frequency component of the phonocardiogram, or a "diaphragm mode" for better capturing a high-frequency component of the phonocardiogram.

Conventional electronic stethoscopes need to process sound data in order to enhance or supplement a medical practitioner's auditory capabilities. However, processing of sound data may introduce a considerable amount of noise into the audio signal which is detrimental to the medical practitioner's ability to recognize potential issues with the patient's organs.

As it will become apparent from the description herein further below, one or more computer-implemented sound filtering procedures may be used in the context of the present technology for processing sound data in the time-domain and/or in the frequency domain. Developers of the present technology have realized that using computer-implemented sound filtering procedures may be less expensive to implement than mechanically-implemented filtering solutions. It is further contemplated that using computer-implemented sound filtering procedures, further allows processing the sound data on any electronic device suitable for running these computer-implemented sound filtering procedures, as opposed to requiring one or more mechanical filters of a particular electronic device.

Developers of the present technology have realized that electronic stethoscopes are expensive at least partially due to the hardware components required for manufacturing such devices. For at least this reason, developers have devised an electronic device that implements various functionalities of electronic stethoscopes.

In at least some embodiments of the present technology, developers have devised computer-implemented methods for processing bodily sounds captured by a mobile phone. In other words, in these embodiments, developers have devised computer-implemented methods for enabling stethoscope functionalities on an "off-the shelf" mobile phone, without any auxiliary hardware equipment.

In a first broad aspect of the present technology, there is provided a method of processing a waveform. The waveform is representative of bodily sounds. The method is executable by an electronic device having a processor. The method comprises acquiring, by the processor, the waveform having a plurality of amplitude data points. The waveform has a low-frequency component and a high-frequency component. The low-frequency component is in a first frequency range and the high-frequency component is in a second frequency range, the second frequency range being above the first frequency range. The method comprises selecting, by the processor, a target moving averaging filter amongst a first moving averaging filter and a second moving averaging filter for filtering the waveform. The first moving averaging filter to be used for preserving the low-frequency component of the waveform. The first moving averaging filter is configured to average a first number of amplitude data points at a given moving iteration. The second moving averaging filter is to be used for preserving the high-frequency component of the waveform. The second moving averaging filter is configured to average a second number of amplitude data points at the given moving iteration. The second number is inferior to the first number. The method comprises applying, by the processor, the target moving averaging filter on the waveform for reducing noise in the waveform, thereby generating a second waveform.

In some embodiments of the method, the method further comprises storing the second waveform in a storage device.

In some embodiments of the method, the electronic device further comprises a sound reproducing component. The method further comprises using, by the processor, the second waveform for reproducing sound by the sound reproducing component.

In some embodiments of the method, the method further comprises applying, by the processor, a cut-off filter on the second waveform for generating a third waveform. The cut-off filter having a cut-off value. The method further comprises re-sampling, by the processor, the third waveform at a pre-determined sampling rate for generating a fourth waveform. The cut-off value being based on the pre-determined sampling rate. The pre-determined sampling rate is below a sampling rate of the sound recording component of the electronic device.

In some embodiments of the method, the method further comprises splitting, by the processor, the fourth waveform into a first temporal segment and a second temporal segment. The first temporal segment has a first maximum amplitude data point. The second temporal segment has a second maximum amplitude data point. The method further comprises normalizing, by the processor, the first temporal segment using the first maximum amplitude data point and the second temporal segment using the second maximum amplitude data point, thereby generating a first normalized temporal segment and a second normalized temporal segment. The method further comprises generating, by the server, a fifth waveform by recombining the first normalized temporal segment and the second normalized temporal segment. The method further comprises providing, by the processor, the fifth waveform to the sound reproducing component of the electronic device for generating sound representative of the fifth waveform.

In some embodiments of the method, the method further comprises acquiring, by the processor, sound data having a first signal in a first channel and a second signal in a second channel and selecting, by the processor, a target channel amongst the first channel and the second channel. The target channel contains information representative of the waveform.

In some embodiments of the method, the selecting comprises comparing, by the processor, an energy of the first signal against an energy of the second signal and selecting, by the processor, the first channel as the target channel if the first signal has a higher energy than the second signal. The first signal is representative of the waveform.

In some embodiments of the method, the selecting comprises comparing, by the processor, a modulus of amplitude of the first signal against a modulus of amplitude of the second signal, and selecting, by the processor, the first channel as the target channel if the first signal has a higher modulus of amplitude than the second signal. The first signal is representative of the waveform.

In some embodiments of the method, one of the first signal and the second signal is a null signal.

In some embodiments of the method, the electronic device is a mobile phone.

In some embodiments of the method, the first number of amplitude data points is a number below 300.

In some embodiments of the method, the first number of amplitude data points is between 100 and 200.

In some embodiments of the method, the second number of amplitude data points is a number below 60.

In some embodiments of the method, the second number of amplitude data points is between 24 and 48.

In some embodiments of the method, the waveform is an audio segment acquired in real-time by the processor, and the second waveform is a second audio segment generated in real-time, and wherein the method further comprises acquiring, by the processor, an other audio segment in real-time, the other audio segment being sequential to the audio segment; applying, by the processor, the target moving averaging filter on the other audio segment for reducing noise in the other audio segment, thereby generating a second other audio segment; and using, by the processor, the second audio segment and the second other audio segment for reproducing sound by the sound reproducing component in real-time.

In a second broad aspect of the present technology, there is provided an electronic device for processing a waveform. The waveform is representative of bodily sounds. The electronic device has a processor. The processor is configured to acquire the waveform from the sound recording component. The waveform has a plurality of amplitude data points. The waveform has a low-frequency component and a high-frequency component. The low-frequency component is a in a first frequency range and the high-frequency component is in a second frequency range. The second frequency range is above the first frequency range. The processor is configured to select a target moving averaging filter amongst a first moving averaging filter and a second moving averaging filter for filtering the waveform. The first moving averaging filter is to be used for preserving the low-frequency component of the waveform. The first moving averaging filter is configured to average a first number of amplitude data points at a given moving iteration. The second moving averaging filter is to be used for preserving the high-frequency component of the waveform. The second moving averaging filter is configured to average a second number of amplitude data points at the given moving iteration. The second number is inferior to the first number. The processor is configured to apply the target moving averaging filter on the waveform for reducing noise in the waveform, thereby generating a second waveform.

In some embodiments of the electronic device, the electronic device is further configured to store the second waveform in a storage device.

In some embodiments of the electronic device, the electronic device comprises a sound reproducing component, and the electronic device is further configured to use the second waveform for reproducing sound by the sound reproducing component.

In some embodiments of the electronic device, the electronic device is further configured to apply a cut-off filter on the second waveform for generating a third waveform, where the cut-off filter has a cut-off value, and re-sample the third waveform at a pre-determined sampling rate for generating a fourth waveform. The cut-off value is based on the pre-determined sampling rate. The pre-determined sampling rate is below a sampling rate of the sound recording component of the electronic device.

In some embodiments of the electronic device, the electronic device is further configured to split the fourth waveform into a first temporal segment and a second temporal segment. The first temporal segment has a first maximum amplitude data point. The second temporal segment has a second maximum amplitude data point. The electronic device is further configured to normalize the first temporal segment using the first maximum amplitude data point and the second temporal segment using the second maximum amplitude data point, thereby generating a first normalized temporal segment and a second normalized temporal segment. The electronic device is further configured to generate a fifth waveform by recombining the first normalized temporal segment and the second normalized temporal segment. The electronic device is further configured to provide the fifth waveform to the sound reproducing component of the electronic device for generating sound representative of the fifth waveform.

In some embodiments of the electronic device, the electronic device is further configured to acquire sound data having a first signal in a first channel and a second signal in a second channel, and select a target channel amongst the first channel and the second channel. The target channel contains information representative of the waveform.

In some embodiments of the electronic device, to select the electronic device is configured to compare an energy of the first signal against an energy of the second signal, and select first channel as the target channel if the first signal has a higher energy than the second signal. The first signal is representative of the waveform.

In some embodiments of the electronic device, to select the electronic device is configured to compare a modulus of amplitude of the first signal against a modulus of amplitude of the second signal, and select the first channel as the target channel if the first signal has a higher modulus of amplitude than the second signal. The first signal is representative of the waveform.

In some embodiments of the electronic device, one of the first signal and the second signal is a null signal.

In some embodiments of the electronic device, the electronic device is a mobile phone.

In some embodiments of the electronic device, the first number of amplitude data points is a number below 300.

In some embodiments of the electronic device, the first number of amplitude data points is between 100 and 200.

In some embodiments of the electronic device, the second number of amplitude data points is a number below 60.

In some embodiments of the electronic device, the second number of amplitude data points is between 24 and 48.

In some embodiments of the electronic device, the waveform is an audio segment acquired in real-time by the processor. The second waveform is a second audio segment generated in real-time. The electronic device is further configured to acquire an other audio segment in real-time, where the other audio segment is sequential to the audio segment. The electronic device is further configured to apply the target moving averaging filter on the other audio segment for reducing noise in the other audio segment, thereby generating a second other audio segment in real-time. The electronic device is further configured to use the second audio segment and the second other audio segment for reproducing sound by the sound reproducing component in real-time.

In a third broad aspect of the present technology, there is provided a method of recording a sound signal by a mobile device. The method comprises determining, by the mobile device, that an edge of the mobile device is biased against a skin of the operator, the mobile device comprising a microphone located on the edge. The method comprises monitoring, by the mobile device, an orientation of the mobile device relative to the skin of the operator. The method comprises in response to the orientation corresponding to a pre-determined orientation, triggering, by the mobile device, recording of bodily sounds using the microphone. The method comprises during recording, monitoring, by the mobile device, at least one parameter amongst (i) an orientation parameter of the mobile device, (ii) a sound parameter of the sound signal, (iii) a pressure parameter of the mobile device. The method comprises in response to the at least one parameter being outside an acceptable range, triggering, by the mobile device, a feedback signal to the operator.

In some embodiments of the method, the method further comprises in response to the orientation not corresponding to the pre-determined orientation, triggering, by the mobile device, an other feedback signal to the operator for adjusting the orientation of the mobile device.

In some embodiments of the method, the feedback signal is at least one of a visual feedback signal and an audio feedback signal.

In the context of the present specification, "electronic device" is any computer hardware that is capable of running software appropriate to the relevant task at hand. Thus, some (non-limiting) examples of client devices include personal computers (desktops, laptops, netbooks, etc.), smartphones, and tablets, as well as network equipment such as routers, switches, and gateways. It should be noted that a device acting as a client device in the present context is not precluded from acting as a server to other client devices. The use of the expression "a client device" does not preclude multiple client devices being used in receiving/sending, carrying out or causing to be carried out any task or request, or the consequences of any task or request, or steps of any method described herein.

In the context of the present specification, a "database" is any structured collection of data, irrespective of its particular structure, the database management software, or the computer hardware on which the data is stored, implemented or otherwise rendered available for use. A database may reside on the same hardware as the process that stores or makes use of the information stored in the database or it may reside on separate hardware, such as a dedicated server or plurality of servers.

In the context of the present specification, the expression "information" includes information of any nature or kind whatsoever capable of being stored in a database. Thus information includes, but is not limited to audiovisual works (images, movies, sound records, presentations etc.), data (location data, numerical data, etc.), text (opinions, comments, questions, messages, etc.), documents, spreadsheets, lists of words, etc.

In the context of the present specification, the expression "component" is meant to include software (appropriate to a particular hardware context) that is both necessary and sufficient to achieve the specific function(s) being referenced.

In the context of the present specification, the expression "computer usable information storage medium" is intended to include media of any nature and kind whatsoever, including RAM, ROM, disks (CD-ROMs, DVDs, floppy disks, hard drivers, etc.), USB keys, solid state-drives, tape drives, etc.

In the context of the present specification, unless expressly provided otherwise, an "indication" of an information element may be the information element itself or a pointer, reference, link, or other indirect mechanism enabling the recipient of the indication to locate a network, memory, database, or other computer-readable medium location from which the information element may be retrieved. For example, an indication of a document could include the document itself (i.e. its contents), or it could be a unique document descriptor identifying a file with respect to a particular file system, or some other means of directing the recipient of the indication to a network location, memory address, database table, or other location where the file may be accessed. As one skilled in the art would recognize, the degree of precision required in such an indication depends on the extent of any prior understanding about the interpretation to be given to information being exchanged as between the sender and the recipient of the indication. For example, if it is understood prior to a communication between a sender and a recipient that an indication of an information element will take the form of a database key for an entry in a particular table of a predetermined database containing the information element, then the sending of the database key is all that is required to effectively convey the information element to the recipient, even though the information element itself was not transmitted as between the sender and the recipient of the indication.

In the context of the present specification, the words "first", "second", "third", etc. have been used as adjectives only for the purpose of allowing for distinction between the nouns that they modify from one another, and not for the purpose of describing any particular relationship between those nouns. Thus, for example, it should be understood that, the use of the terms "first server" and "third server" is not intended to imply any particular order, type, chronology, hierarchy or ranking (for example) of/between the server, nor is their use (by itself) intended imply that any "second server" must necessarily exist in any given situation. Further, as is discussed herein in other contexts, reference to a "first" element and a "second" element does not preclude the two elements from being the same actual real-world element. Thus, for example, in some instances, a "first" server and a "second" server may be the same software and/or hardware, in other cases they may be different software and/or hardware.

Implementations of the present technology each have at least one of the above-mentioned object and/or aspects, but do not necessarily have all of them. It should be understood that some aspects of the present technology that have resulted from attempting to attain the above-mentioned object may not satisfy this object and/or may satisfy other objects not specifically recited herein.

Additional and/or alternative features, aspects and advantages of implementations of the present technology will become apparent from the following description, the accompanying drawings and the appended claims.

BRIEF DESCRIPTION OF THE DRAWINGS

For a better understanding of the present technology, as well as other aspects and further features thereof, reference is made to the following description which is to be used in conjunction with the accompanying drawings, where.

DETAILED DESCRIPTION

Figure 1:
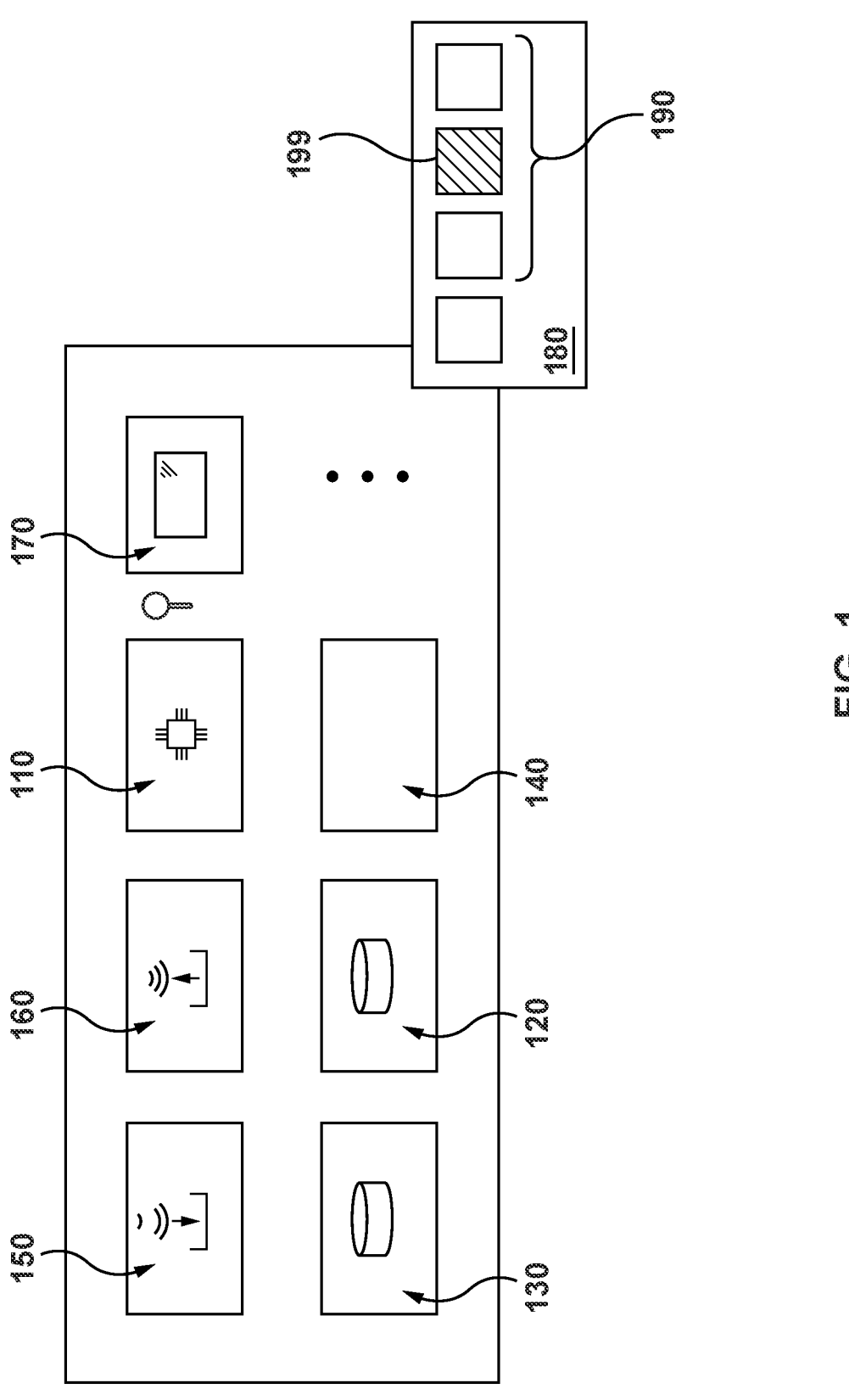
FIG. 1 depicts a computer system suitable for use with some non-limiting embodiments of the present technology.

The examples and conditional language recited herein are principally intended to aid the reader in understanding the principles of the present technology and not to limit its scope to such specifically recited examples and conditions. It will be appreciated that those skilled in the art may devise various arrangements which, although not explicitly described or shown herein, nonetheless embody the principles of the present technology and are included within its spirit and scope.

Furthermore, as an aid to understanding, the following description may describe relatively simplified implementations of the present technology. As persons skilled in the art would understand, various implementations of the present technology may be of a greater complexity.

In some cases, what are believed to be helpful examples of modifications to the present technology may also be set forth. This is done merely as an aid to understanding, and, again, not to define the scope or set forth the bounds of the present technology. These modifications are not an exhaustive list, and a person skilled in the art may make other modifications while nonetheless remaining within the scope of the present technology. Further, where no examples of modifications have been set forth, it should not be interpreted that no modifications are possible and/or that what is described is the sole manner of implementing that element of the present technology.

Moreover, all statements herein reciting principles, aspects, and implementations of the present technology, as well as specific examples thereof, are intended to encompass both structural and functional equivalents thereof, whether they are currently known or developed in the future. Thus, for example, it will be appreciated by those skilled in the art that any block diagrams herein represent conceptual views of illustrative circuitry embodying the principles of the present technology. Similarly, it will be appreciated that any flowcharts, flow diagrams, state transition diagrams, pseudo-code, and the like represent various processes which may be substantially represented in computer-readable media and so executed by a computer or processor, whether or not such computer or processor is explicitly shown.

The functions of the various elements shown in the figures, including any functional block labeled as a "processor" or a "graphics processing unit", may be provided through the use of dedicated hardware as well as hardware capable of executing software in association with appropriate software. When provided by a processor, the functions may be provided by a single dedicated processor, by a single shared processor, or by a plurality of individual processors, some of which may be shared. In some embodiments of the present technology, the processor may be a general purpose processor, such as a central processing unit (CPU) or a processor dedicated to a specific purpose, such as a graphics processing unit (GPU). Moreover, explicit use of the term "processor" or "controller" should not be construed to refer exclusively to hardware capable of executing software, and may implicitly include, without limitation, digital signal processor (DSP) hardware, network processor, application specific integrated circuit (ASIC), field programmable gate array (FPGA), read-only memory (ROM) for storing software, random access memory (RAM), and non-volatile storage. Other hardware, conventional and/or custom, may also be included.

Software modules, or simply modules which are implied to be software, may be represented herein as any combination of flowchart elements or other elements indicating performance of process steps and/or textual description. Such modules may be executed by hardware that is expressly or implicitly shown.

With these fundamentals in place, we will now consider some non-limiting examples to illustrate various implementations of aspects of the present technology.

Computer System

Referring initially to FIG. 1, there is depicted a computer system 100 suitable for use with some implementations of the present technology, the computer system 100 comprising various hardware components including one or more single or multi-core processors collectively represented by a processor 110, a solid-state drive 120, a memory 130, which may be a random-access memory or any other type of memory. Communication between the various components of the computer system 100 may be enabled by one or more internal and/or external buses (not shown) (e.g. a PCI bus, universal serial bus, IEEE 1394 "Firewire" bus, SCSI bus, Serial-ATA bus, etc.), to which the various hardware components are electronically coupled.

In at least some embodiments of the present technology, the solid-state drive 120 stores program instructions suitable for being loaded into the memory 130 and executed by the processor 110 for performing time-domain processing of sound data. For example, the program instructions may be part of a time-domain processing application executable by the processor 110.

In some non-limiting embodiments of the present technology, the computer system 100 comprises a sound-detecting component 150. For example, the sound-detecting component 150 may be implemented as one or more microphones configured to detect, and capture sound (e.g., bodily sounds of a given patient) in any suitable audio format. That is, the sound-detecting component 150 can be said to detect sound and generate a waveform signal representative of that sound for further use thereof. Also, the computer system 100 comprises a sound-reproducing component 160. For example, the sound-reproducing component 160 may be implemented as one or more speakers configured to acquire sound data and reproduce sound (e.g., to be heard by a medical practitioner). That is, the sound-reproducing component 160 can be said to receive a waveform signal and use it for generating an audible representation thereof to a given user.

In at least some embodiments of the present technology, it is contemplated that the computer system 100 may have additional and/or optional components, such as a network communication module 140 for communication, with other electronic devices and/or servers, localization modules (not depicted), and the like.

It is contemplated that the computer system 100 includes suitable hardware for running a variety of computer programs 180. For example, the computer system 100 may be configured to execute a plurality of applications 190. Broadly speaking, an application program ("app" or application for short) is a computer program designed to carry out a specific task other than one relating to the operation of the computer system 100 itself, typically to be used by end-users. Applications may be bundled with the computer system 100 and its system software and/or published separately. The term "app" often refers to applications for mobile devices such as smartphones.

It should be noted that the computer system 100 may be configured to run and/or execute a sound processing application 199. How the sound processor application 199 may be implemented in at least some embodiments of the present technology will be described in greater details herein further below.

Figure 2:
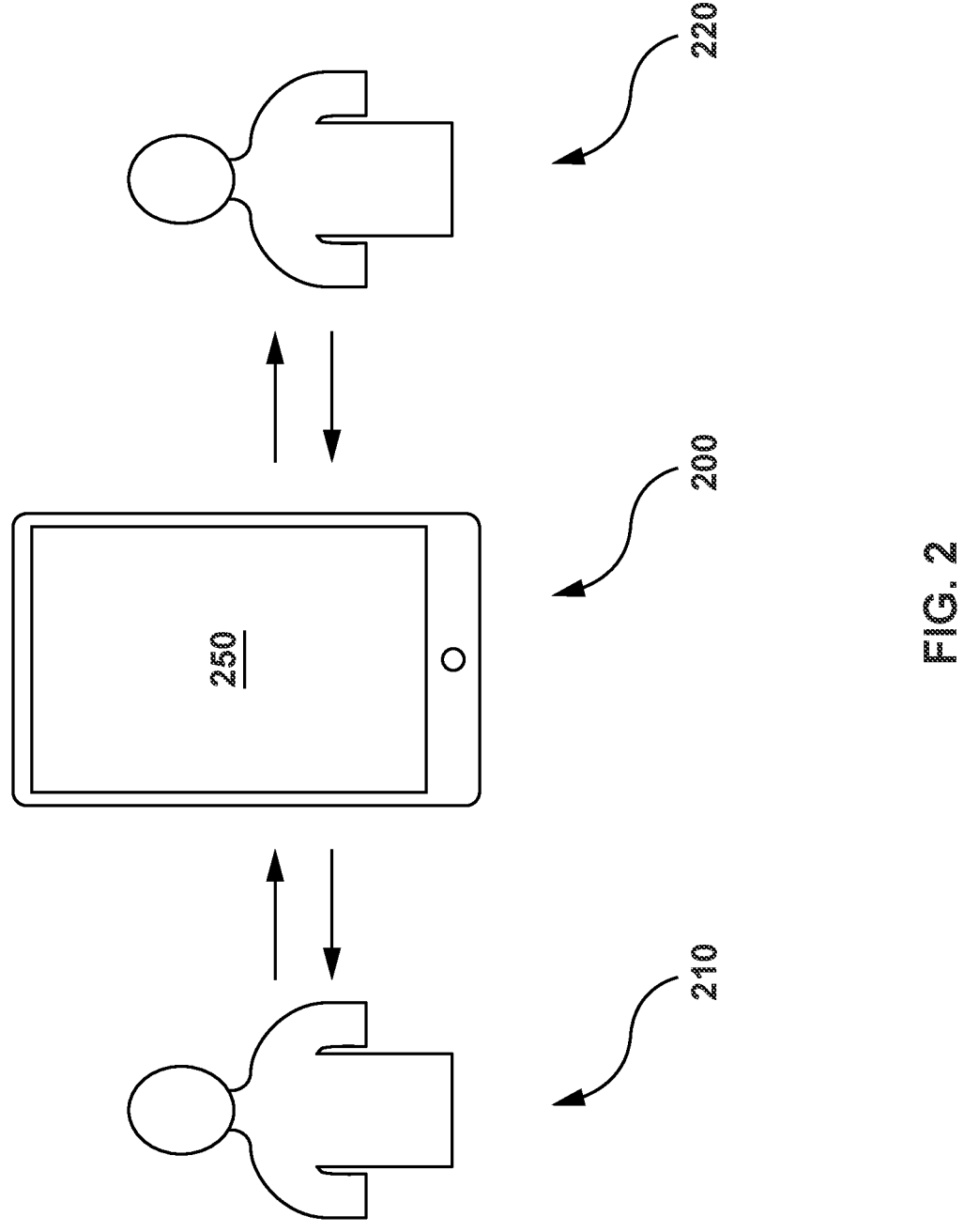
FIG. 2 depicts a representation of an electronic device for processing a waveform signal, in accordance with at least some non-limiting embodiments of the present technology.

With reference to FIG. 2, there is depicted a representation 200 of an electronic device 250 in accordance with at least some non-limiting embodiments of the present technology. How the electronic device 250 is implemented is not particularly limiting. However, just as an example, the electronic device 250 may comprise one or more components of the computer system 100 illustrated in FIG. 1.

In some embodiments of the present technology, the electronic device 250 may be implemented as an "off-the-shelf" smartphone, without any auxiliary equipment. In one implementation of the present technology, the electronic device 250 may be a Samsung™ Galaxy A71 smartphone. In another implementation, the electronic device 250 may be an Apple™ iPhone 11 smartphone.

For example, as illustrated in FIG. 2, a medical practitioner 220 may use the off-the-shelf smartphone to capture sound from a patient's 210 body, which then processes the sound, and provides an enhanced representation of that sound to the medical practitioner 220. It is contemplated that the medical practitioner 220 may be a human operator of the electronic device 250.

Nevertheless, it should be noted that the electronic device 250 being a given off-the-shelf smartphone is only one non-limiting implementation of the present technology.

In one non-limiting implementation of the present technology, the electronic device 250 may be implemented as an electronic stethoscope. Broadly speaking, a given electronic stethoscope is an electronic medical instrument for listening to the action of a user's heart or breathing. Typically, they include a computer system for inter alia sound data processing, a small disc-shaped resonator to be placed against the chest of a patient for capturing sound, and earpieces for reproducing sound to a user of the electronic stethoscope.

In other embodiments, the electronic device 250 may be implemented as any electronic device suitable for processing a waveform signal associated with the patient 210 for generating a modified waveform signal via execution of one or more computer-implemented procedures described herein. For example, the electronic device 250 may also be implemented as a personal computer, a laptop, a server, a communication device, a wearable device, or the like, without departing from the scope of the present technology.

Figure 3:
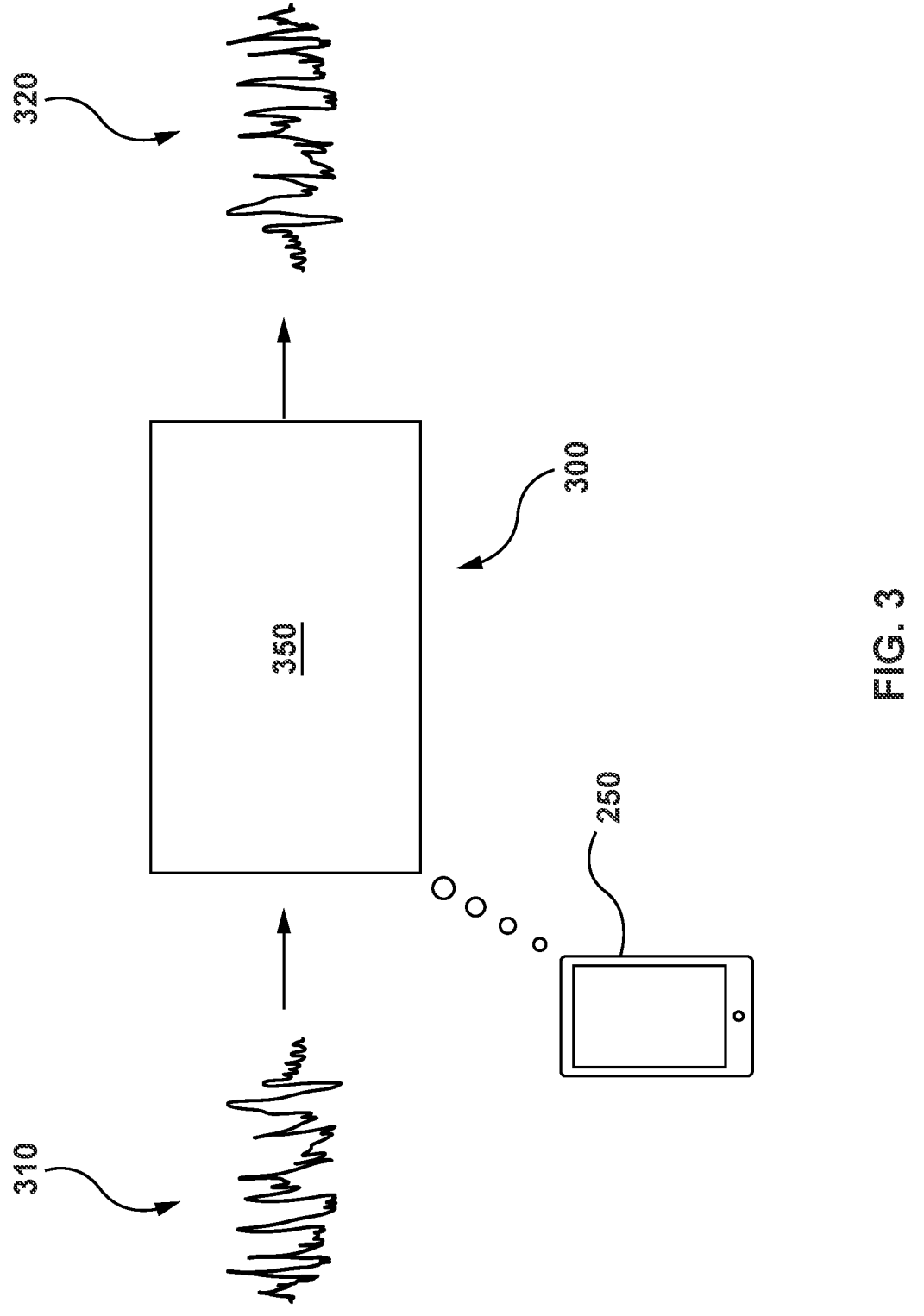
FIG. 3 depicts a representation of how the electronic device of FIG. 2 generates a modified waveform signal based on a waveform signal, in accordance with at least some non-limiting embodiments of the present technology.

With reference to FIG. 3, there is depicted a representation 300 of how the electronic device 250 of FIG. 2 generates a modified waveform signal 320 based on a respective waveform signal 310 associated with the patient 210. As illustrated and previously alluded to, the electronic device 250 is configured to execute a plurality of sound processing computer-implemented procedures 350 in order to process the waveform signal 310.

How the plurality of sound processing computer-implemented procedures 350 are executed by the electronic device

250, in some embodiments of the present technology, will be described in greater detail herein further below with reference to FIG. 5. However, it should be noted that the purpose of the plurality of sound processing computer-implemented procedures 350 is to generate the modified waveform signal 320 that can enhance and/or supplement auditory capabilities of the medical practitioner 220. How the medical practitioner 220 may be configured to employ the electronic device 250 for acquiring the waveform 310 will now be described.

Acquisition of Waveform for Processing

In some embodiments of the present technology, a user of the electronic device 250 such as the medical practitioner 220 may launch the sound processing application 199 on the electronic device 250. The electronic device 205 may be configured to display an interface for the medical practitioner 220 indicating a type of auscultation to be performed. For example, the interface may allow the medical practitioner 220 to select a "heart" auscultation mode, a "lung" auscultation mode, and the like.

Additionally or alternatively, the default auscultation mode may be automatically selected by the electronic device 250. In such cases, the medical practitioner 220 may still be able to change a target auscultation mode from the default mode to one other auscultation mode, without departing from the scope of the present technology.

Once the selection is made, the electronic device 250 may be configured to provide visual instructions to the medical practitioner 220 for placement of the electronic device 250 against the skin of the patent 210. It should be noted that in some embodiments of the present technology, a user may use the electronic device 250 for recording his own bodily sounds, without departing from the scope of the present technology.

Figure 4:
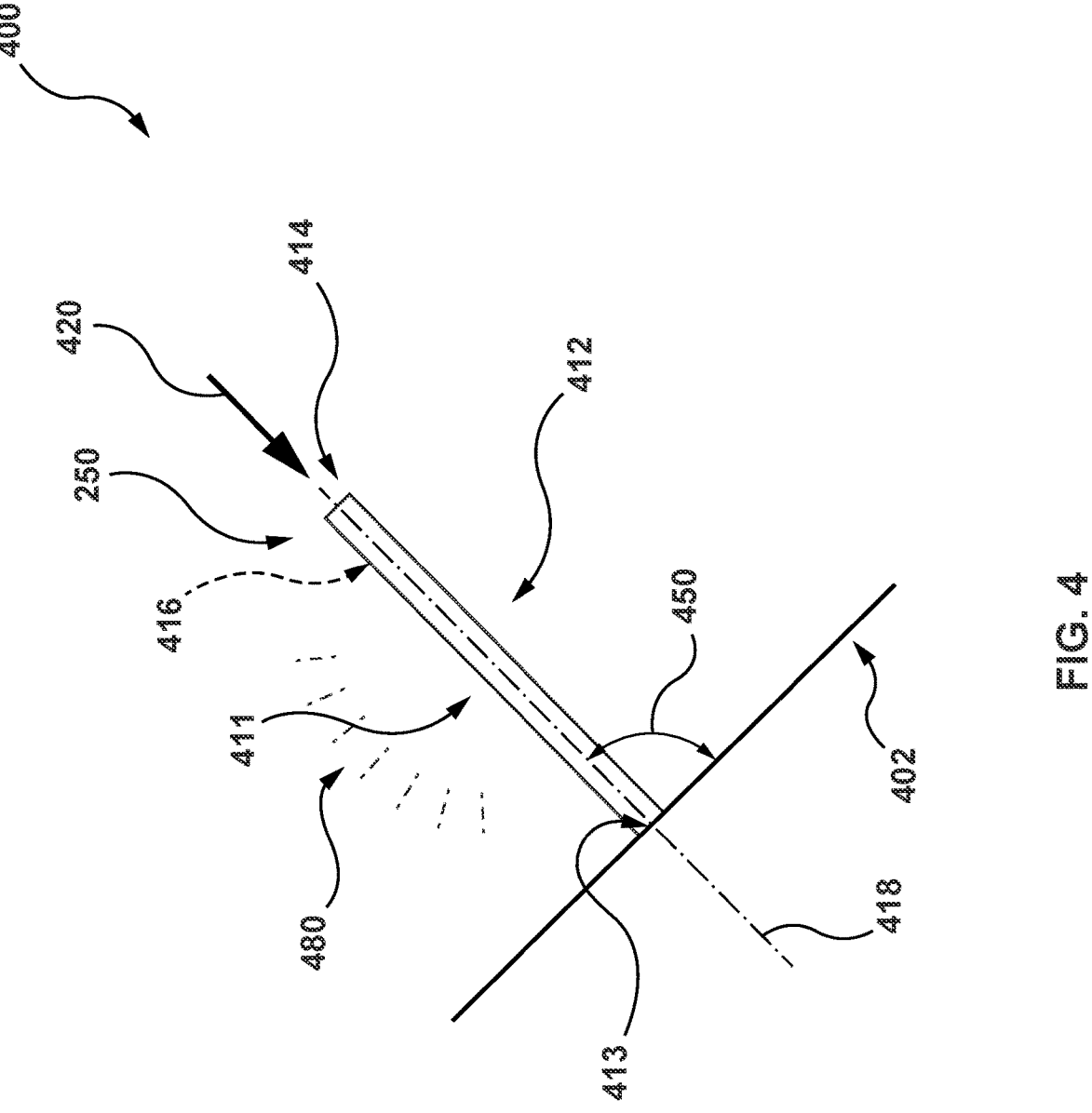
FIG. 4 is a schematic illustration of how the electronic device of FIG. 2 is biased against a skin surface for acquiring the waveform signal, in one non-limiting implementation of the present technology.

With reference to FIG. 4, there is depicted a schematic representation 400 of how the electronic device 250 can be placed against the skin of the patient 210 in some implementations of the present technology.

As illustrated, the electronic device 250 has a top surface 411 with a display 416, a back surface 412, a microphone surface 413, and an opposite surface 414 to the microphone surface 413. The user can bias the electronic device 250 against a skin surface 402 of the patient 210 by applying a force 420 onto the opposite surface 414. The force 420 may be applied using one or more fingers of the medical practitioner 220.

It should be noted that when the microphone surface 413 is so-biased against the skin surface 402, the electronic device 250 is positioned at an angle 450 from the skin surface 402. The angle 450 is an angle between a longitudinal axis 418 of the electronic device 250 and the skin surface 402. In one implementation of the present technology, the electronic device 250 may be placed at a 90-degree angle relative to the skin surface 402 of the patient 210.

It should be noted that so-positioning the electronic device 210 relative to the skin surface 402 and biasing the microphone surface 413 against the skin surface 402 may allow to create a "seal" between the skin and the microphone surface 413 for better capturing bodily sounds by the microphone. It some embodiments, it can be said that biasing the microphone surface 413 against the skin surface 402 may allow substantially isolating the microphone from ambient noise.

Let it be assumed that the user selected the "heart" auscultation mode. In such a case, the microphone may be turned on for detecting the heartbeat of the patient 210 while the electronic device 210 is in position as depicted in FIG.

4. In response to detecting the heartbeat, the electronic device 250 may trigger recording of a signal representative of bodily sounds (e.g., heart sounds) of the patient 210. In other embodiments, the electronic device 250 may provide an actuatable element via the display 416 for allowing the user to trigger recording of the said signal. Optionally, signals from one or more other sensors (e.g., pressure sensors) of the electronic device 250 may be used for triggering the recording.

During the recording of a waveform, the electronic device 250 may be configured to provide visual feedback to the user via the display 416 for adjusting the position and/or orientation of the electronic device 250 relative to the skin surface 402. For example, instructions for adjusting the position and/or orientation of the electronic device 250 may be generated based on data from one or more components of the electronic device 250.

In one embodiment, data from a gyroscope and/or an accelerometer of the electronic device 250 may be used for generating instructions for the user to adjust the current position and/or orientation of the electronic device 250. In another embodiment, sound data from an auxiliary microphone of the electronic device 250 may be used for comparing an amplitude of the ambient sound against the amplitude of a real-time segment of the waveform representative of bodily sounds. Depending on this comparison, the electronic device 250 may generate instructions for the user to adjust the current position and/or orientation of the electronic device 250.

In one implementation, the electronic device 250 may be configured to stop acquisition of the waveform (e.g., stop recording) after 20 seconds. In another implementation, the electronic device may be configured to stop acquisition of the waveform if no adjustment of the position and/or orientation of the electronic device 250 was requested from the user within the last 20 seconds. It is also contemplated that the user may manually trigger the recording to be stopped without departing from the scope of the present technology.

In some embodiments, the electronic device 250 may be configured to store and/or process the waveform once it has been recorded. In other words, the electronic device 250 may perform post-acquisition processing of the waveform representative of bodily sounds. In other embodiments, however, the waveform may be processed in "real-time" as the waveform is being recorded.

For example, the electronic device 250 may be configured to process respective real-time segments of the waveform as they are being recorded, thereby generating corresponding real-time processed segments of the modified waveform to be provided to the user of the electronic device 250. In these embodiments, it is contemplated that the electronic device 250 may reproduce a modified waveform to the user in real-time (via wireless headphones, for example), as the electronic device 250 is recording the bodily sounds of the patient. It can be said that the electronic device 250 may operate in a "real-time configuration" for reproducing a modified waveform to the user simultaneously during acquisition of the waveform representative of bodily sounds.

How the electronic device 250 may be configured to process a waveform in post-acquisition configuration and/or real-time segments of the waveform in real-time configuration will now be described in greater detail.

Processing of Waveform

Figure 5:
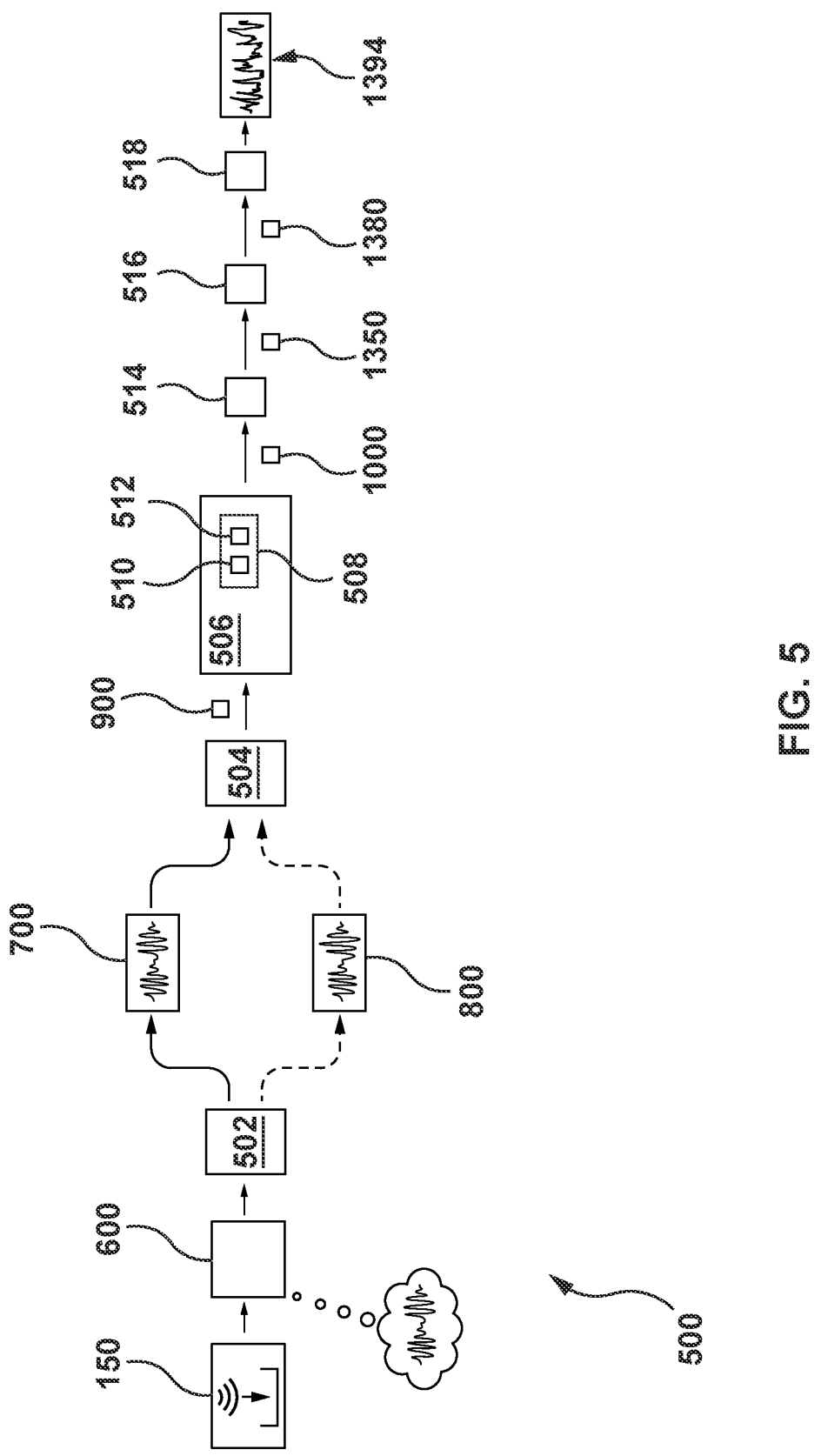
FIG. 5 is a schematic illustration of processing performed by the electronic device of FIG. 2 for generating the modified waveform signal based on the waveform signal.
Figure 6:
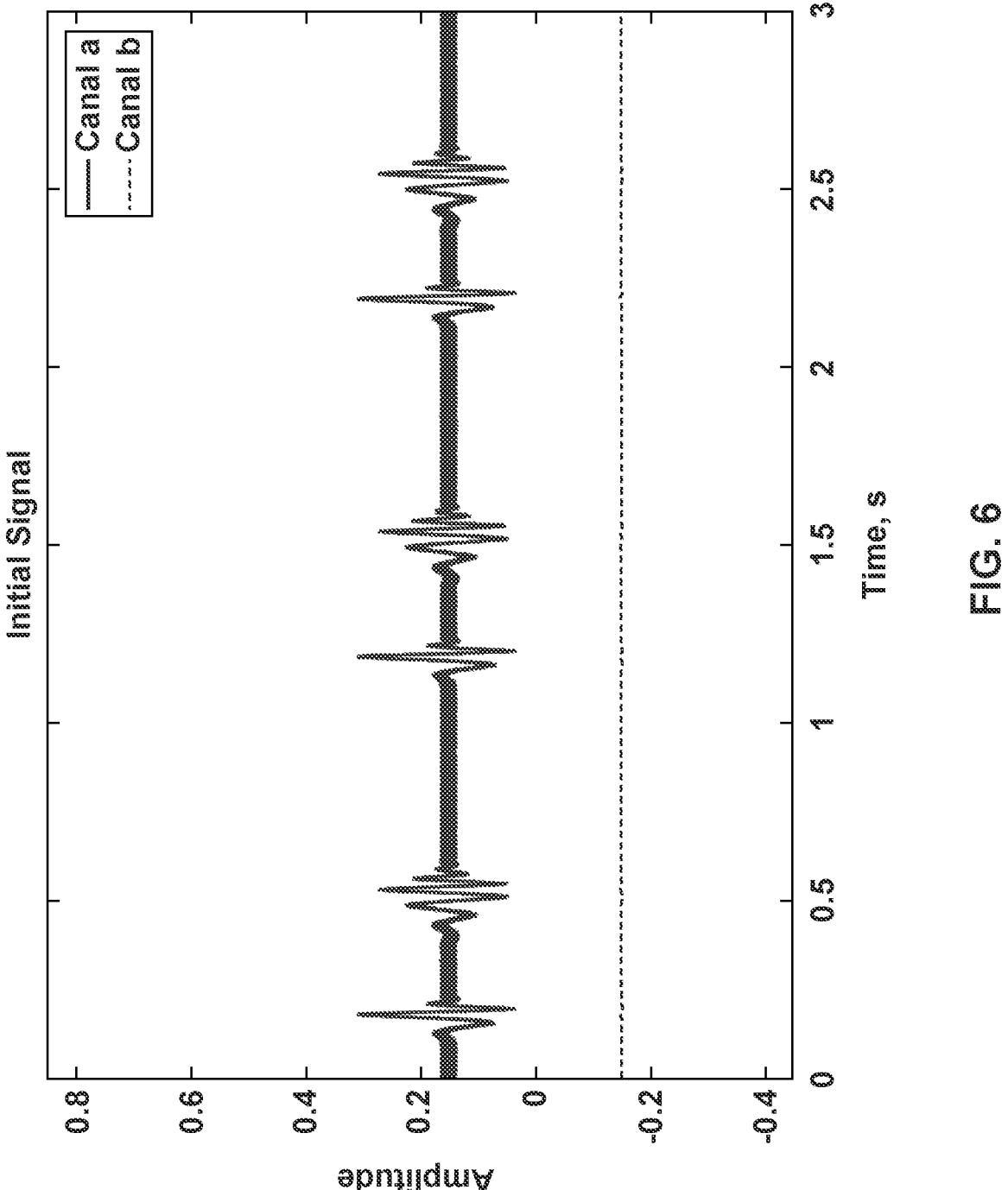
FIG. 6 is a non-limiting example of sound data captured by the electronic device of FIG. 2.

With reference to FIG. 5, there is depicted a schematic representation of a process 500 executable by the processor 110 of the electronic device 250 for processing a waveform. For example, the electronic device 250 may be used to generate sound data 600 representative of sound captured by one or more sound detection component(s) 150. A non-limiting example of the sound data 600 is depicted in FIG. 6.

It should be noted that the signal 600 can have a first channel "a" carrying a first signal 602 and a second channel "b" carrying a second signal 604. For example, the electronic device 250 may have two microphones and the first signal 602 may be representative of sound captured by a main microphone and the second signal 602 may be representative of sound captured by an auxiliary microphone.

Figure 7:
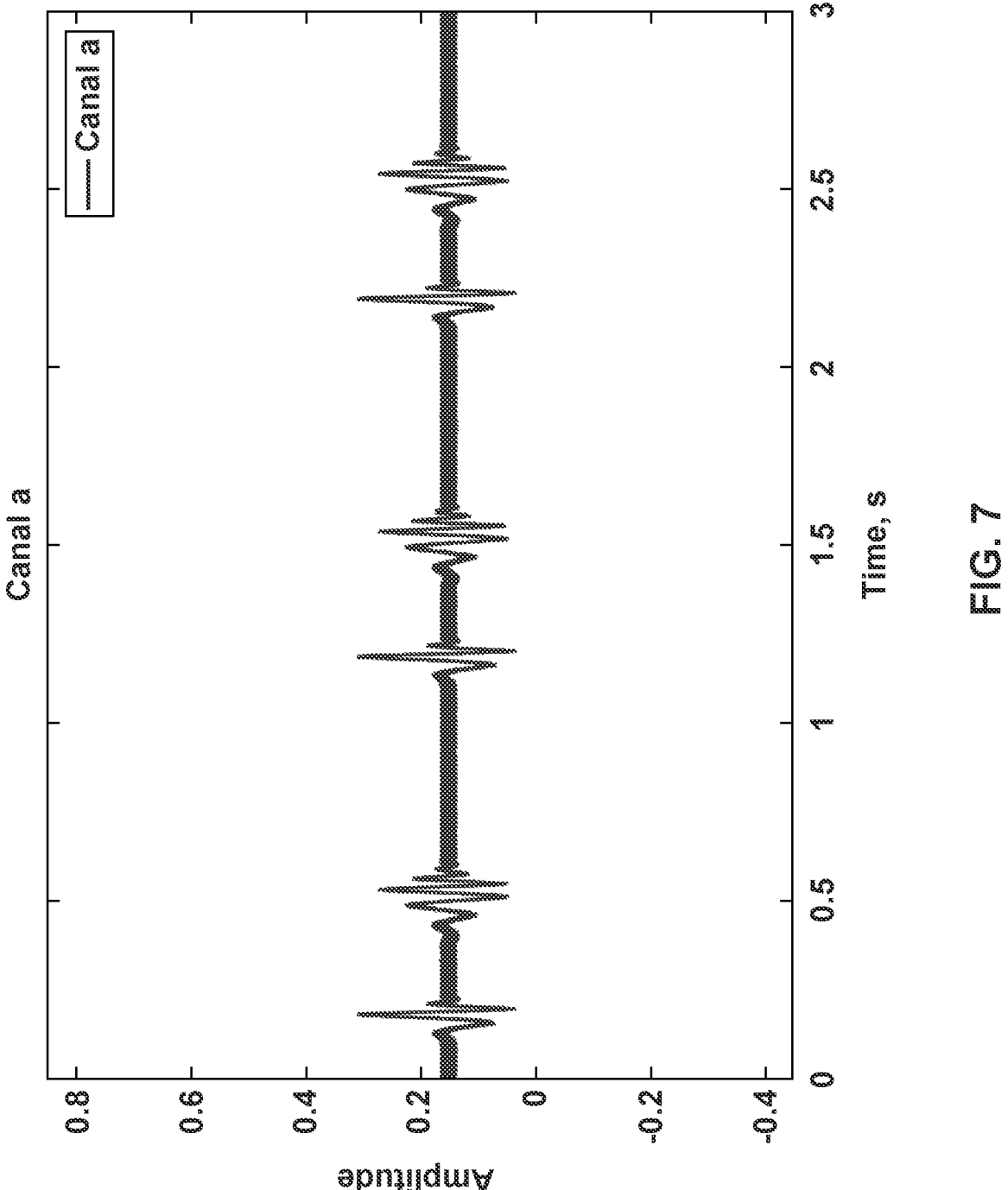
FIG. 7 is a non-limiting example of a waveform from a first channel of the sound data of FIG. 6.
Figure 8:
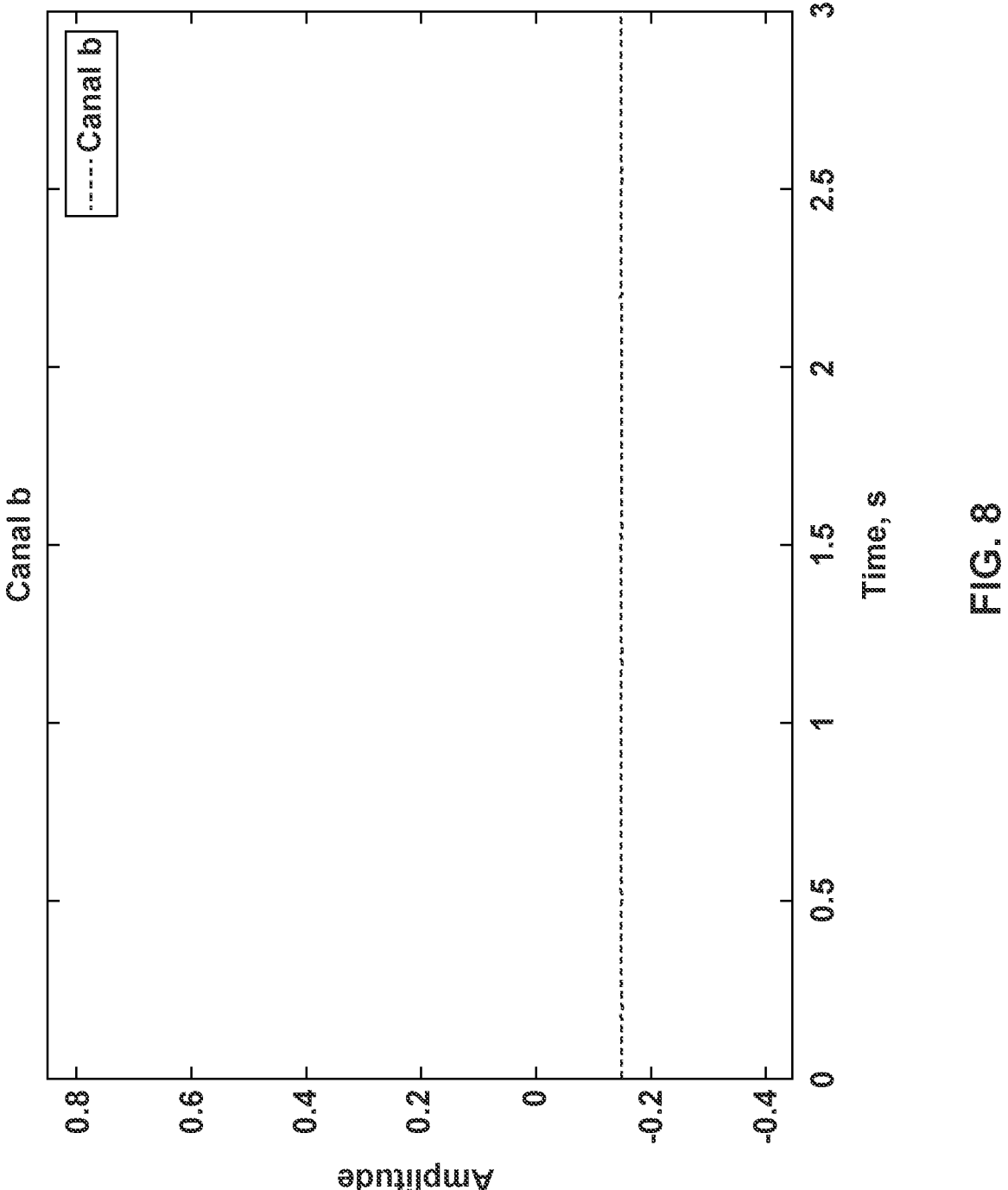
FIG. 8 is a non-limiting example of a waveform from a second channel of the sound data of FIG. 6.

In some embodiments, the processor 110 may be configured to perform a channel separation procedure 502 in order to split the first signal 602 and the second signal 604. In these embodiments, the processor 110 may generate a pair of waveforms including a waveform 700 corresponding to the first signal 602 and a waveform 800 corresponding to the second signal 604. Non-limiting examples of the waveform 700 and of the waveform 800 are depicted in FIGS. 7 and 8, respectively.

In those embodiments where the sound data 600 has more than one channel, the processor 110 may be configured to select a target channel amongst the first channel a and the second channel b for further processing. In other words, the processor 110 may be configured to select one of the waveforms 700 and 800 as a given waveform to be used for further processing in the process 500.

To that end, the processor 110 may be configured to input both the waveforms 700 and 800 into a channel selection procedure 504. Broadly speaking, the channel selection procedure 504 is configured to compare one or more characteristics of the waveforms 700 and 800 and determine which one of the waveforms 700 and 800 are to be used for further processing in the process 500.

In one embodiment of the present technology, the processor 110 executing the channel selection procedure 504 may be configured to compare the energy of the waveform 700 against the energy of the waveform 800. Optionally, the processor 110 executing the channel selection procedure 504 may be configured to compare the energy of at least one segment of the waveform 700 against the energy of at least one segment of the waveform 800.

In another embodiment of the present technology, the processor 110 executing the channel selection procedure 504 may be configured to compare a modulus of amplitude of the waveform 700 against a modulus of amplitude of the waveform 800. Optionally, the processor 110 executing the channel selection procedure 504 may be configured to compare the modulus of amplitude of at least one segment of the waveform 700 against the modulus of amplitude of at least one segment of the waveform 800.

The processor 110 may determine that a given one of the waveforms 700 and 800 associated with a comparatively higher value of energy and/or modulus of amplitude is to be selected for further processing. Alternatively, instead of inputting the waveforms 700 and 800 into the channel selection procedure 504, the processor 110 may be configured to input the waveform 600 itself and perform comparison of one or more characteristics of the respective signals included in the waveform 600.

Figure 9:
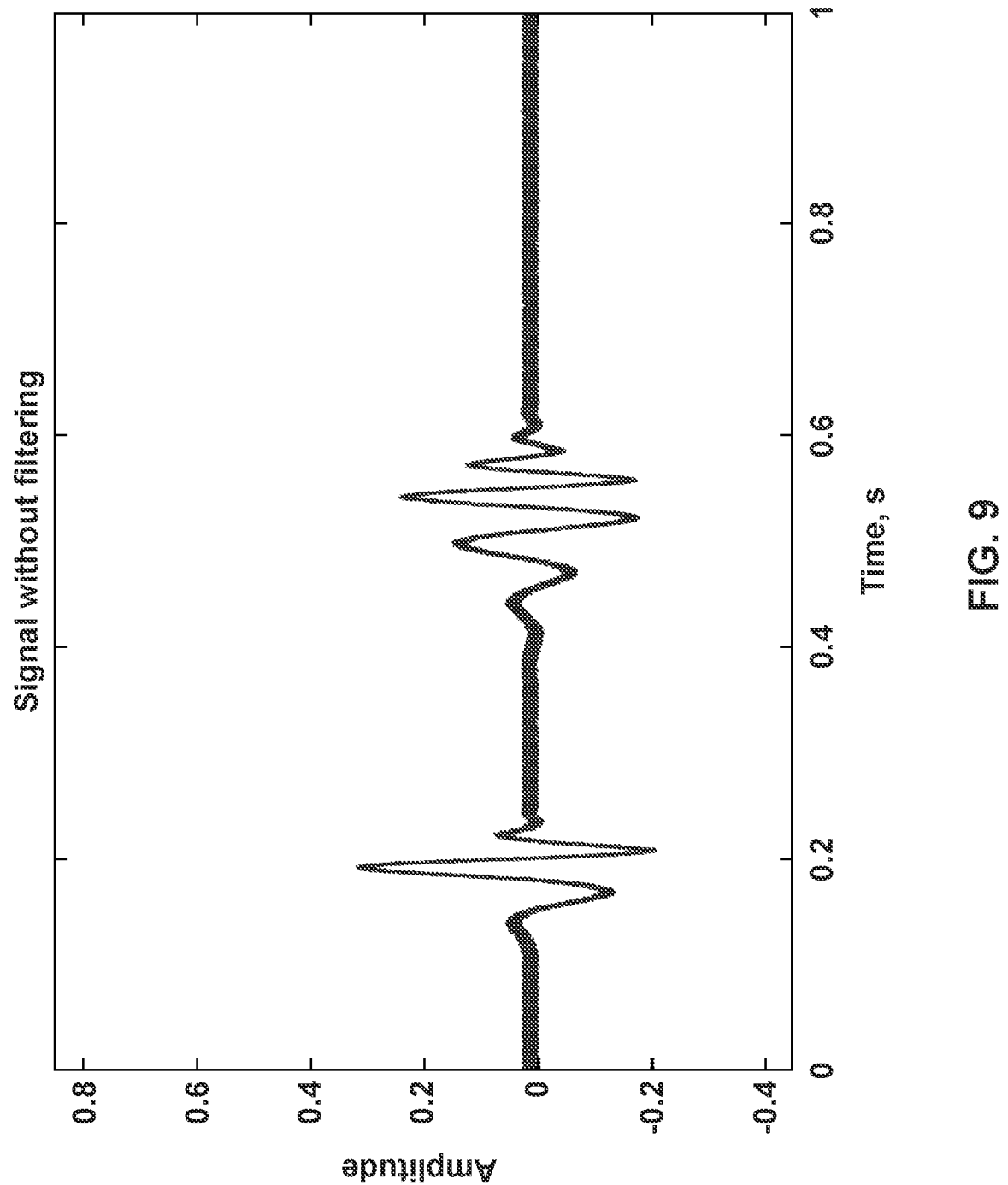
FIG. 9 is a zoomed-in representation of the waveform of FIG. 7

In the non-limiting example illustrated in FIG. 8, the waveform 800 corresponds to a null signal. This may be the case for a variety of reasons. In at least some embodiments of the present technology, it may be advantageous to turn off the auxiliary microphone during the recording of the bodily sounds by the electronic device 250. In this case, a channel corresponding to this auxiliary microphone may contain a null signal, while a channel corresponding to the main microphone may contain the signal to be used for further processing. In this case, the channel selection algorithm 504 may compare the total energies and/or amplitudes of the respective signals for making the selection. With reference to FIG. 9, there is depicted a zoomed-in representation of the waveform 700 that can be selected by the processor 110 for further processing, in one implementation of the present technology.

In other implementations of the present technology, both the main and auxiliary microphones may be turned on for recording the bodily sounds by the electronic device 250. In this case, following the selection of one of the signals for further processing based on a comparison of total energies and/or amplitudes, the other one of the two signals may also be used during processing of the selected signal. In one embodiment, it is contemplated that the selected signal may be carrying information about bodily sounds while the other signal may be used for filtering out ambient noise from the selected signal.

Returning to the description of FIG. 5, the processor 110 may be configured to perform a plurality of filtering operations 506 on the waveform 700. More particularly, in the context of the present technology, the processor 110 may be configured to apply one or more from a plurality of moving averaging filters 508. Broadly speaking, the moving average filter is a filter that the processor 110 may use for regulating an array of a sampled signal. The processor 110 may use such a filter to (i) take a number M of samples of input at a time, (ii) average these samples, and (iii) produce a single output point. It is contemplated that as the size/length of the filter increases, the smoothness of the output may increase, such that sharp modulations in the data are made increasingly blunt. In one implementation, a moving averaging filter may be a Low Pass Finite Impulse Response (LPFIR) filter.

It should be noted that the plurality of moving averaging filters 508 comprises a first moving averaging filter 510 and a second moving averaging filter 512. The first moving averaging filter 510 is configured to average a first number of amplitude data points at a given iteration. In some implementations, the first moving averaging filter 510 may be configured to average between "100" and "200" amplitude data points at a given iteration. In other implementations, the first moving averaging filter 510 may be configured to average less than "300" amplitude data points at a given iteration.

The second moving averaging filter 512 is configured to average a second number of amplitude data points at a given iteration. In some implementations, the second moving averaging filter 512 may be configured to average between 24 and 48 amplitude data points at a given iteration. In other implementations, the second moving averaging filter 512 may be configured to average less than 60 amplitude data points at a given iteration.

It should be noted that the processor 110 is configured to select one of the plurality of moving averaging filters 512 for filtering the waveform 900. Developers of the present technology have realized that the first moving averaging filter 510 may be used for preserving the low-frequency component of the waveform 700, and the second moving averaging filter 512 may be used for preserving the high-frequency and the low-frequency components of the waveform 700. It can be said that the second moving averaging filter 512 may be used for preserving at least the high-frequency component of the waveform 700.

In some embodiments of the present technology, the processor 110 may be configured to select a target one amongst the first moving averaging filter 510 and the second moving averaging filter 512 depending on inter alia a target stethoscopic mode of operation.

Figure 10:
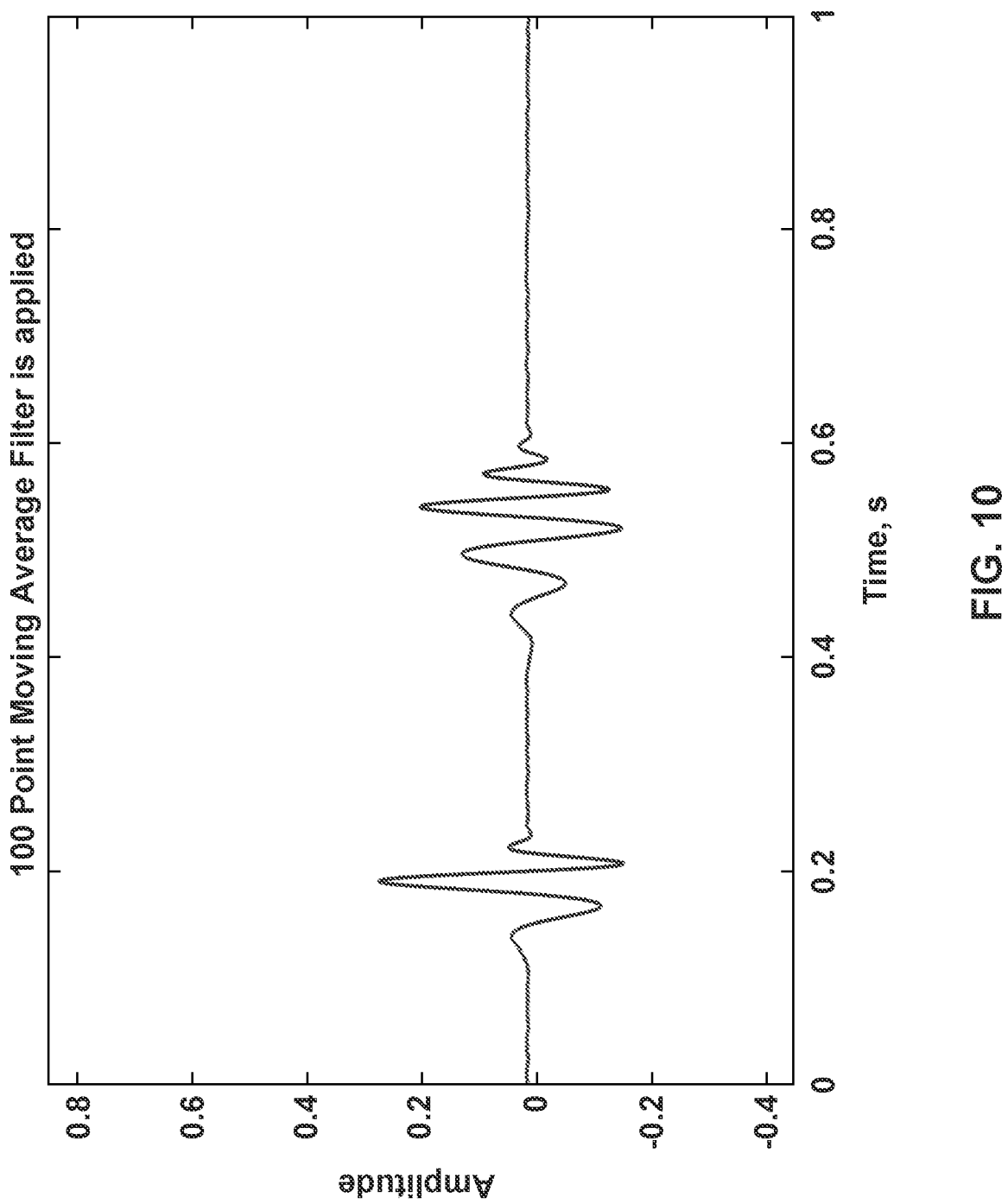
FIG. 10 is a non-limiting example of a waveform generated by applying a first moving averaging filter onto the waveform of FIG. 7.
Figure 11:
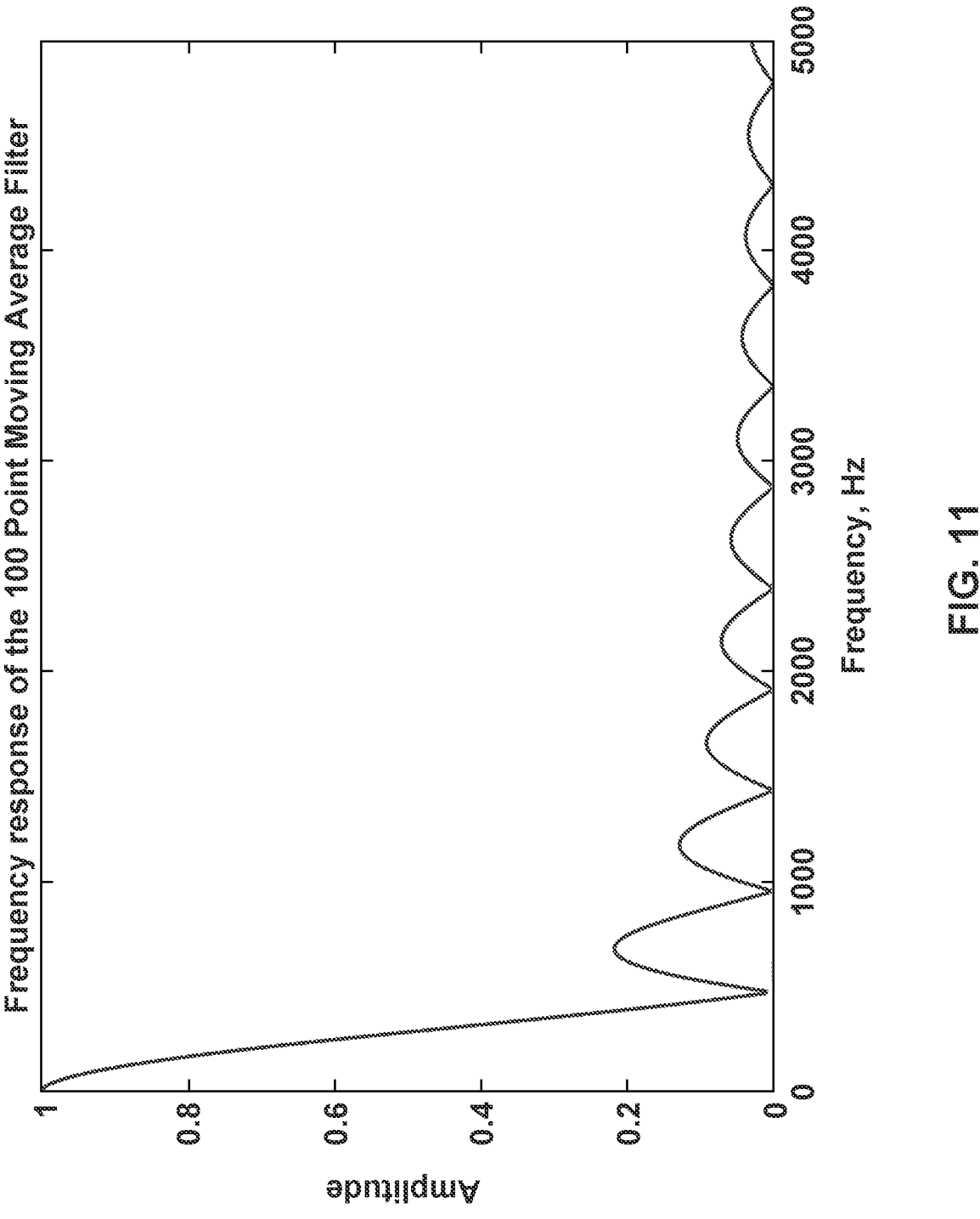
FIG. 11 is a non-limiting example of the frequency response of the waveform of FIG. 10.

For example, if the target mode of operation is a "bell" mode, the processor 110 may be configured to select the first moving averaging filter 510 as the target moving averaging filter. In this example, the low-frequency component of the waveform 700 may be preserved for generating the modified waveform under the bell mode of operation. In this example, the processor 110 is configured to apply the first moving averaging filter 510 on the waveform 700, thereby generating a waveform 1000. A non-limiting example of the waveform 1000 is depicted in FIG. 10. A non-limiting example of the frequency response of the waveform 1000 is depicted in FIG. 11.

Figure 12:
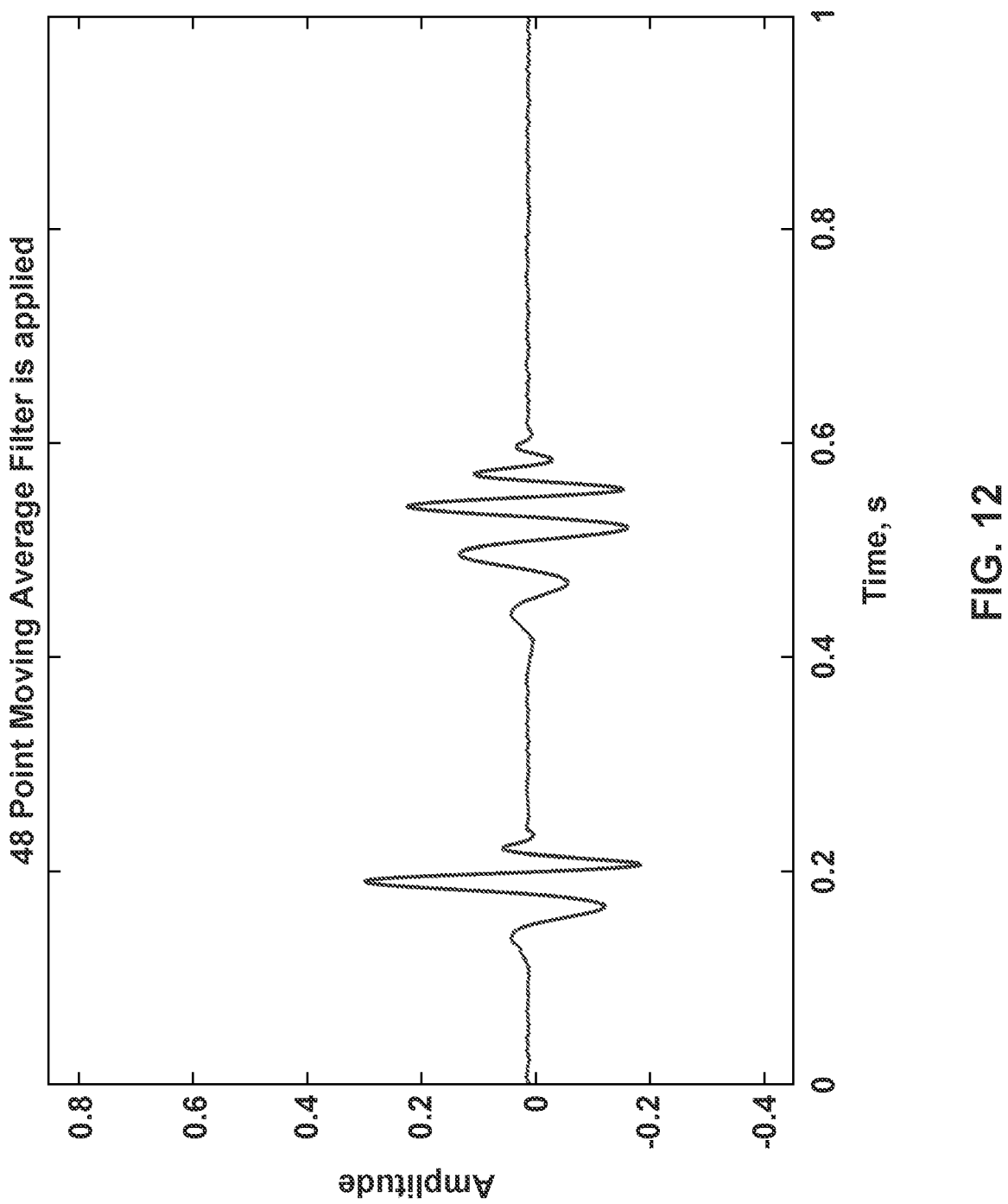
FIG. 12 is a non-limiting example of a waveform generated by applying a second moving averaging filter onto the waveform of FIG. 7.
Figure 13:
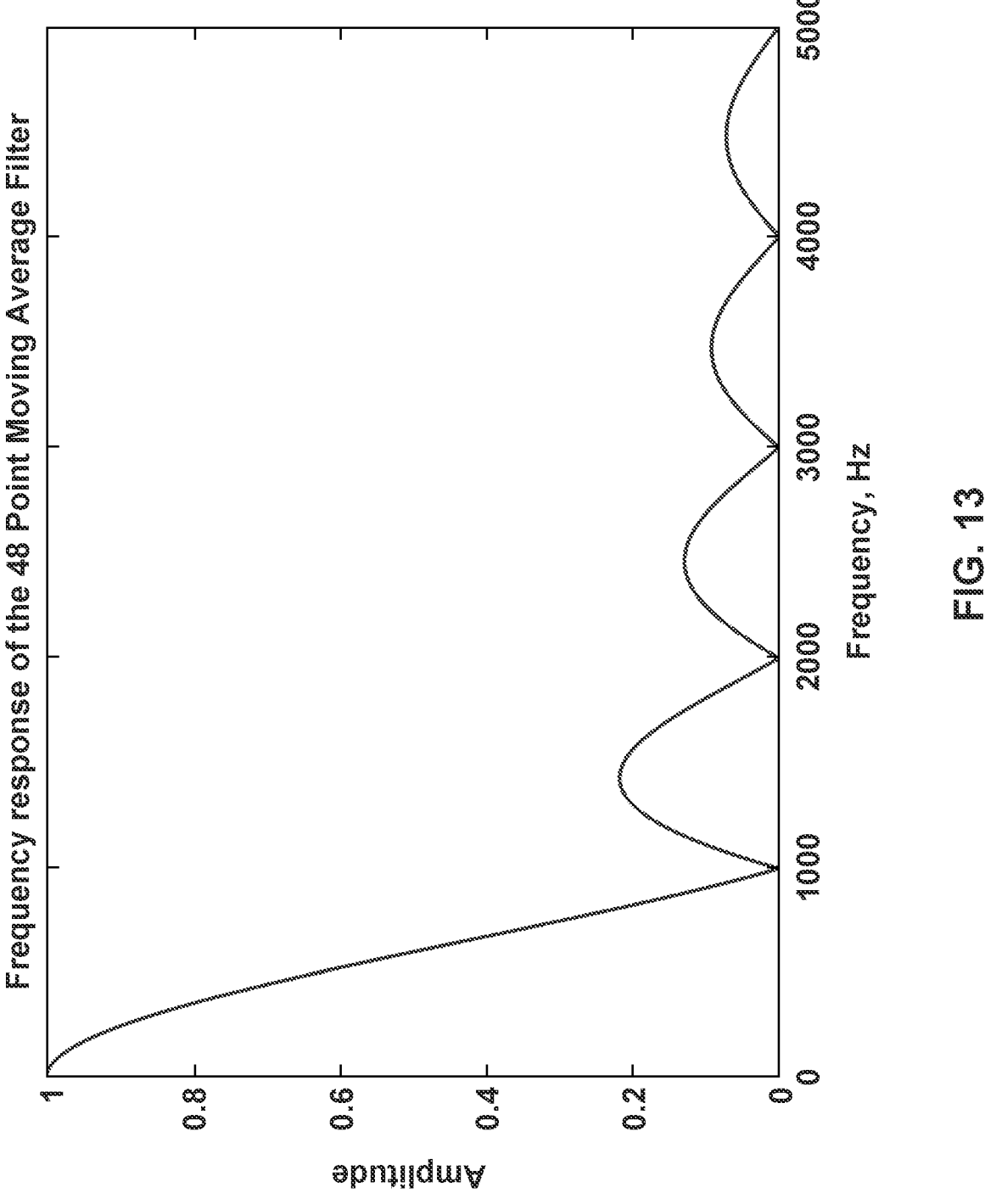
FIG. 13 is a non-limiting example of the frequency response of the waveform of FIG. 12.

In another example, if the target mode of operation is a "diaphragm" mode, the processor 110 may be configured to select the second moving averaging filter 512 as the target moving averaging filter. In this example, high-frequency and the low-frequency components of the waveform 700 may be preserved. Then, the low-frequency component may be filter out via an additional filter for retaining only the high-frequency component for generating the modified waveform under the diaphragm mode of operation. In this other example, the processor 110 is configured to apply the second moving averaging filter 512 on the waveform 700, thereby generating a waveform 1200. A non-limiting example of the waveform 1200 is depicted in FIG. 12. A non-limiting example of the frequency response of the waveform 1200 is depicted in FIG. 13.

Let it be assumed that the processor 110 generates the waveform 1000. In one embodiment, the electronic device 210 may apply a cut-off filter 514 on the waveform 1000 for generating a waveform 1350. Additionally or optionally, the processor 110 may be configured to perform a re-sampling procedure 516 by re-sampling the waveform 1350 at a pre-determined sampling rate, thereby generating a waveform 1380.

In some embodiments, a cut-off value of the cut-off filter 514 may be based on the pre-determined sampling rate. The pre-determined sampling rate may be below a sampling rate of the sound recording component of the electronic device 250. In one implementation, the cut-off filter has a cut-off value of 2 kHz. In this implementation, the pre-determined sampling rate may be 4 kHz.

In some embodiments, the processor 110 is configured to perform a normalization procedure 518 on the waveform 1380. As part of the normalization procedure 518, the processor 110 may be configured to split the waveform 1380 into a plurality of temporal segments for independently adjusting their amplitudes.

For example, the processor 110 may be configured to split the waveform 1380 into a first temporal segment and a second temporal segment. The processor 110 may identify a first maximum amplitude data point in the first temporal segment, and a second maximum amplitude data point in the second temporal segment. The processor 110 may also be configured to normalize the first temporal segment using the first maximum amplitude data point and the second temporal segment using the second maximum amplitude data point, thereby generating a first and a second normalized temporal segments. The processor 110 may then recombine the first and second normalized temporal segments for generating a waveform 1399. It is contemplated that the processor 110 may be configured to split the waveform 1380 into a plurality of segments. In some embodiments the time duration of these segments may be between 0.5 and 3 seconds each.

It is contemplated that independent adjustment of temporal segments in a waveform may allow compensating for inadvertent movement of the electronic device 250 relative to the body surface of the patient during acquisition of corresponding temporal segment of the waveform.

It is contemplated that the waveform 1400 may be stored and/or provided to the sound reproducing component 160 for reproducing sound for a medical practitioner representative of the waveform 1399.

Figure 14:
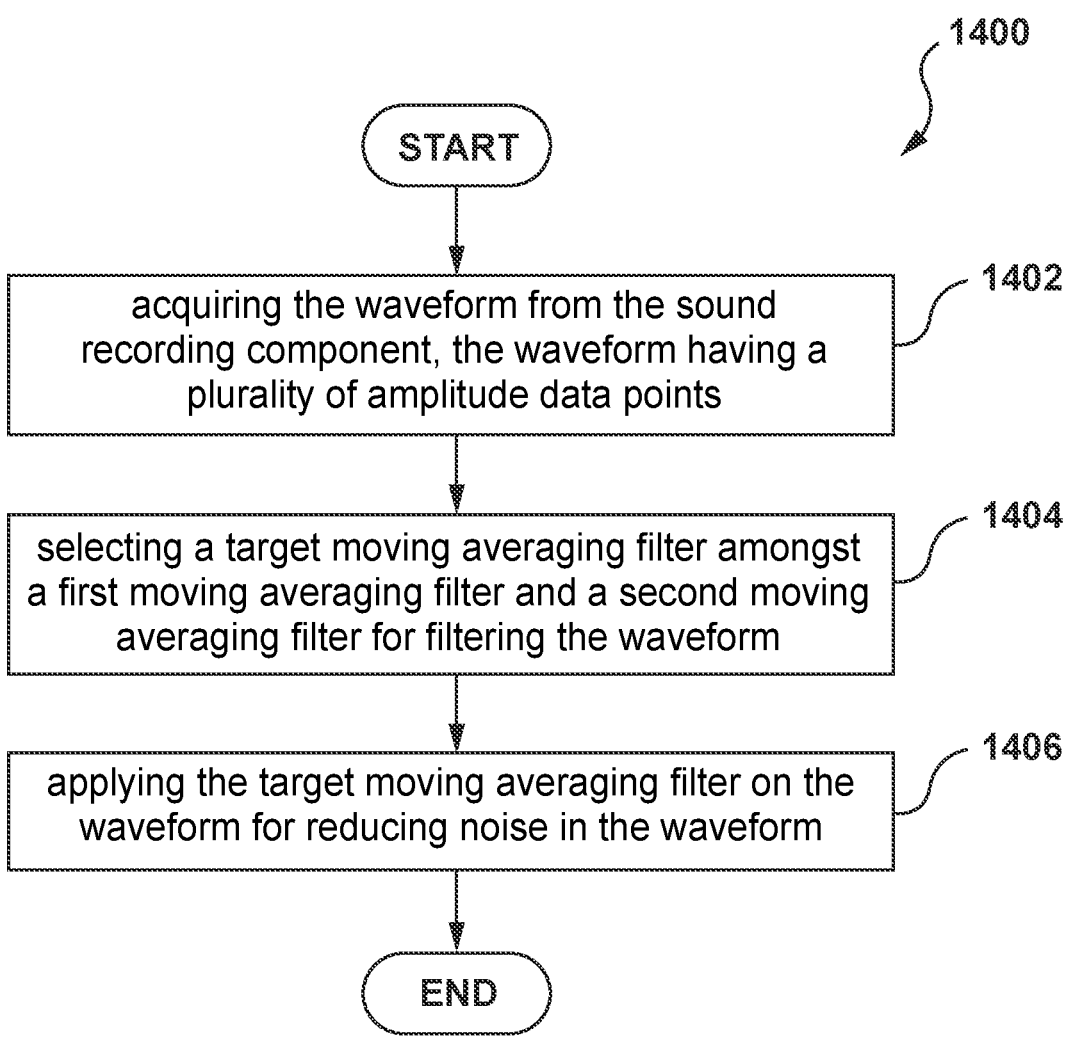
FIG. 14 is a schematic diagram of a method executable by a processor of FIG. 1, in accordance with at least some non-limiting embodiments of the present technology.

In some embodiments of the present technology, the processor 110 of FIG. 1 may be configured to execute a method 1400 depicted in FIG. 14. Various steps of the method 14 will now be described in turn.

Step 1402: Acquiring the Waveform Having a Plurality of Amplitude Data Points

The method 1400 begins at step 1402 with the processor 110 of the electronic device 250 configured to acquire a waveform having a plurality of amplitude data points. In some embodiments, the waveform acquired by the processor 110 may be the waveform 700.

In other embodiments, the processor 110 may be configured to acquire sound data having a first signal in a first channel and a second signal in a second channel and select a target channel amongst the first channel and the second channel where the target channel contains information representative of the waveform 700.

The processor 110 may perform channel selection in a variety of ways. In some embodiments, the processor 110 may compare an energy of the first signal against an energy of the second signal and select the first channel as the target channel if the first signal has a higher energy than the second signal. In other embodiments, the processor 110 may compare a modulus of amplitude of the first signal against a modulus of amplitude of the second signal and select the first channel as the target channel if the first signal has a higher modulus of amplitude than the second signal. It is contemplated that one of the first signal and the second signal may be a null signal.

It should be noted that the waveform 700 has a low-frequency component and a high-frequency component. The low-frequency component is in a first frequency range and the high-frequency component is in a second frequency range. The second frequency range is above the first frequency range. In on example, the low-frequency component may be in a frequency range between 0 Hz and 163 Hz, while the high-frequency component may be in a frequency rage between 163 Hz and 1000 Hz.

Step 1404: Selecting a Target Moving Averaging Filter Amongst a First Moving Averaging Filter and a Second Moving Averaging Filter for Filtering the Waveform The method 1400 continues to step 1404 with the processor 110 of the electronic device 250 configured to select a target moving averaging filter amongst the first moving averaging filter 510 and the second moving averaging filter 512.

The first moving averaging filter 510 is to be used for preserving the low-frequency component of the waveform 700 and is configured to average a first number of amplitude data points at a given moving iteration. The second moving averaging filter is to be used for preserving at least the high-frequency component of the waveform 700 and is configured to average a second number of amplitude data points at the given moving iteration. The second number is inferior to the first number.

In some embodiments, the selection of the target moving averaging filter may depend on inter alia a stethoscopic mode of operation selected by the user. For example, if the stethoscopic mode of operation is the "bell" mode, the processor 110 may be configured to select the first moving averaging filter 510 as the target moving averaging filter. In another example, if the stethoscopic mode of operation is the "diaphragm" mode, the processor 110 may be configured to select the second moving averaging filter 512 as the target moving averaging filter.

In some embodiments, the first number of amplitude data points may be a number below 300. In other embodiments, the first number of amplitude data points may be between 100 and 200. In further embodiments, the second number of amplitude data points may be a number below 60. In additional embodiments, the second number of amplitude data points may be between 24 and 48.

Step 1406: Applying the Target Moving Averaging Filter on the Waveform for Reducing Noise in the Waveform The method 1400 continues to step 1406 configured to apply the target moving averaging filter on the waveform 700 for reducing noise in the waveform.

For example, if the first moving averaging filter 510 is the target moving averaging filter, the low-frequency component of the waveform 700 may be preserved for generating the modified waveform under the bell mode of operation. In this example, the processor 110 is configured to apply the first moving averaging filter 510 on the waveform 700, thereby generating the waveform 1000.

For example, if the second moving averaging filter 512 is the target moving averaging filter, the high-frequency and the low-frequency components of the waveform 700 may be preserved. Then, the low-frequency component may be filter out via an additional filter for retaining only the high-frequency component for generating the modified waveform under the diaphragm mode of operation. In this other example, the processor 110 is configured to apply the second moving averaging filter 512 on the waveform 700, thereby generating the waveform 1200.

In some embodiments, the processor 110 may store at least one of the waveform 1000 and the waveform 1200 in a stored device (e.g., in memory) for further use thereof.

In other embodiments, the processor 110 may use at least one of the waveform 1000 and the waveform 1200 for reproducing sound by the sound reproducing component 160. It is contemplated that further processing may be performed on at least one of the waveform 1000 and the waveform 1200 prior to reproducing sound via the sound reproducing component 160.

In one embodiment, the processor 110 may apply the cut-off filter 514 on at least one of the waveform 1000 and the waveform 1200 for generating another waveform. The processor 110 may also re-sample the other waveform at a pre-determined sampling rate for generating a further waveform. It should be noted that in some embodiments, the cut-off filter 514 and the re-sampling procedure 516 may be linked together in the sense that the cut-off value of the cut-off filter 514 may be based on the pre-determined sampling rate.

In another embodiment, the processor 110 may be configured to split the further waveform into a first temporal segment and a second temporal segment (and/or a plurality of temporal segments). The first temporal segment has a first maximum amplitude data point and the second temporal segment has a second maximum amplitude data point. The processor 110 may normalize the first temporal segment using the first maximum amplitude data point and the second temporal segment using the second maximum amplitude data point, thereby generating a first normalized temporal segment and a second normalized temporal segment. The processor 110 may also generate a waveform by recombining the first normalized temporal segment and the second normalized temporal segment and provide this waveform to the sound reproducing component 160 of the electronic device 250 for generating sound for the user.

It is further contemplated that the waveform processing described herein may be performed in real-time. For example, respective real-time waveform segments representative of bodily sounds may be processed as they are recorded, and the processed versions thereof may be reproduced in real-time to the user.

In some embodiments, the electronic device 250 may be configured to process respective real-time segments of the waveform as they are being recorded, thereby generating corresponding real-time processed segments of the modified waveform to be provided to the user of the electronic device 250. In these embodiments, it is contemplated that the electronic device 250 may reproduce a modified waveform to the user in real-time (via wireless headphones, for example), as the electronic device 250 is recording the bodily sounds of the patient. It can be said that the electronic device 250 may operate in a "real-time configuration" for reproducing a modified waveform to the user simultaneously during acquisition of the waveform representative of bodily sounds.

In the real-time configuration, the waveform 700 may be an audio segment acquired in real-time by the processor 110, and at least one of the waveform 1000 and the waveform 1200 is an audio segment generated in real-time. In this configuration, the processor 110 may acquire an other audio segment in real-time that is sequential to the audio segment, apply the target moving averaging filter on the other audio segment for reducing noise in the other audio segment, thereby generating a second other audio segment and use both processed real-time audio-segments for reproducing sound by the sound reproducing component 160 in real-time.

It should be expressly understood that not all technical effects mentioned herein need to be enjoyed in each and every embodiment of the present technology. For example, embodiments of the present technology may be implemented without the user enjoying some of these technical effects, while other embodiments may be implemented with the user enjoying other technical effects or none at all.

Some of these steps and signal sending-receiving are well known in the art and, as such, have been omitted in certain portions of this description for the sake of simplicity. The signals can be sent-received using optical means (such as a fibre-optic connection), electronic means (such as using wired or wireless connection), and mechanical means (such as pressure-based, temperature based or any other suitable physical parameter based).

Modifications and improvements to the above-described implementations of the present technology may become apparent to those skilled in the art. The foregoing description is intended to be exemplary rather than limiting. The scope of the present technology is therefore intended to be limited solely by the scope of the appended claims.

The invention claimed is:

1. A method of recording a sound signal by a mobile device, comprising:

determining, by the mobile device, that an edge of the mobile device is biased against a skin of an operator, the mobile device comprising a microphone located on the edge;

monitoring, by the mobile device, an orientation of the mobile device relative to the skin of the operator;

in response to the orientation corresponding to a pre-determined orientation, triggering, by the mobile device, recording of bodily sounds using the microphone;

during recording, monitoring, by the mobile device, at least one parameter amongst (i) an orientation parameter of the mobile device, (ii) a sound parameter of the sound signal, (iii) a pressure parameter of the mobile device;

in response to the at least one parameter being outside an acceptable range, triggering, by the mobile device, a feedback signal to the operator;

selecting a first moving average filter or a second moving average filter for applying to the recording, wherein the first moving average filter is configured to average a first amount of amplitude data points at a moving iteration, and wherein the second moving average filter is configured to average a second amount of amplitude data points at the moving iteration, the second amount being different from the first amount; and applying the selected moving average filter to the recording.

2. The method of claim 1, wherein the method further comprises:

in response to the orientation not corresponding to the pre-determined orientation, triggering, by the mobile device, another feedback signal to the operator for adjusting the orientation of the mobile device.

3. The method of claim 1, wherein the feedback signal is at least one of a visual feedback signal and an audio feedback signal.

4. The method of claim 1, wherein the mobile device includes a display.

5. A method of recording a sound signal by a mobile phone, comprising:

determining, by the mobile phone, that an edge of the mobile phone is biased against a skin of an operator, the mobile phone comprising a microphone located on the edge;

monitoring, by the mobile phone, an orientation of the mobile phone relative to the skin of the operator;

in response to the orientation corresponding to a pre-determined orientation, triggering, by the mobile phone, recording of the sound signal using the microphone, wherein the sound signal is a heart sound signal or a lung sound signal;

during recording, monitoring, by the mobile phone, at least one parameter amongst (i) an orientation parameter of the mobile phone, (ii) a sound parameter of the sound signal, (iii) a pressure parameter of the mobile phone;

in response to the at least one parameter being outside an acceptable range, triggering, by the mobile phone, a feedback signal to the operator;

selecting a first moving average filter or a second moving average filter for applying to the recording, wherein the first moving average filter is configured to average a first amount of amplitude data points at a moving iteration, and wherein the second moving average filter is configured to average a second amount of amplitude data points at the moving iteration, the second amount being different from the first amount; and applying the selected moving average filter to the recording.

6. The method of claim 5, wherein the method further comprises:

in response to the orientation not corresponding to the pre-determined orientation, triggering, by the mobile phone, another feedback signal to the operator for adjusting the orientation of the mobile phone.

7. The method of claim 5, wherein the feedback signal is at least one of a visual feedback signal and an audio feedback signal.

8. The method of claim 5, wherein the mobile phone includes a display.

9. The method of claim 1, wherein the method further comprises:

comparing the at least one parameter against the acceptable range after the recording has ended; and triggering the feedback signal after the recording has ended.

10. The method of claim 5, wherein the method further comprises:

comparing the at least one parameter against the acceptable range after the recording has ended; and triggering the feedback signal after the recording has ended.

11. The method of claim 1, wherein the microphone is substantially isolated from an ambient noise when the orientation of the mobile device corresponds to the pre-determined orientation.

12. The method of claim 1, wherein a seal between the skin and a microphone surface is formed if the orientation corresponds to the pre-determined orientation.

13. A mobile device comprising a microphone located on an edge of the mobile device, at least one processor, and at least one memory comprising executable instructions which, when executed by the at least one processor, cause the mobile device to:

determine that the edge of the mobile device is biased against a skin of an operator;

monitor an orientation of the mobile device relative to the skin of the operator;

in response to the orientation corresponding to a pre-determined orientation, trigger recording of bodily sounds using the microphone, wherein the microphone is substantially isolated from an ambient noise when the orientation of the mobile device corresponds to the pre-determined orientation;

during recording, monitor at least one parameter amongst (i) an orientation parameter of the mobile device, (ii) a sound parameter of a sound signal of the recording, (iii) a pressure parameter of the mobile device;

in response to the at least one parameter being outside an acceptable range, trigger a feedback signal to the operator;

select a first moving average filter or a second moving average filter for applying to the recording, wherein the first moving average filter is configured to average a first amount of amplitude data points at a moving iteration, and wherein the second moving average filter is configured to average a second amount of amplitude data points at the moving iteration, the second amount being different from the first amount; and apply the selected moving average filter to the recording.

14. The mobile device of claim 13, wherein the executable instructions further cause the mobile device to, in response to the orientation not corresponding to the pre-determined orientation, trigger, another feedback signal to the operator for adjusting the orientation of the mobile device.

15. The mobile device of claim 13, wherein the feedback signal is at least one of a visual feedback signal and an audio feedback signal.

16. The mobile device of claim 13, further comprising a display.

17. The mobile device of claim 13, wherein the executable instructions further cause the mobile device to:

compare the at least one parameter against the acceptable range after the recording has ended; and trigger the feedback signal after the recording has ended.

* * * * *